United States Patent
Hung et al.

(10) Patent No.: US 9,655,909 B2
(45) Date of Patent: May 23, 2017

(54) PERSONALIZED MEDICINE FOR THE PREDICTION OF THERAPY TARGETING THE HEDGEHOG PATHWAY

(71) Applicant: Board of Regents, The University of Texas System, Austin, TX (US)

(72) Inventors: Mien-Chie Hung, Houston, TX (US); Yan Wang, Houston, TX (US); Jaffer Ajani, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 118 days.

(21) Appl. No.: 14/371,062

(22) PCT Filed: Jan. 14, 2013

(86) PCT No.: PCT/US2013/021401
§ 371 (c)(1),
(2) Date: Jul. 8, 2014

(87) PCT Pub. No.: WO2013/106812
PCT Pub. Date: Jul. 18, 2013

(65) Prior Publication Data
US 2015/0017651 A1   Jan. 15, 2015

Related U.S. Application Data

(60) Provisional application No. 61/585,872, filed on Jan. 12, 2012, provisional application No. 61/591,034, filed on Jan. 26, 2012.

(51) Int. Cl.
| | |
|---|---|
| A61K 31/4355 | (2006.01) |
| A61K 31/436 | (2006.01) |
| A61K 31/439 | (2006.01) |
| A61K 31/44 | (2006.01) |
| A61K 31/517 | (2006.01) |
| A61K 31/53 | (2006.01) |
| A61K 31/5377 | (2006.01) |
| A61K 31/675 | (2006.01) |
| A61K 45/06 | (2006.01) |
| A61K 31/438 | (2006.01) |
| A61K 31/4402 | (2006.01) |
| A61K 31/4433 | (2006.01) |
| A61K 31/52 | (2006.01) |
| G01N 33/53 | (2006.01) |
| C12N 15/113 | (2010.01) |

(52) U.S. Cl.
CPC .......... *A61K 31/675* (2013.01); *A61K 31/436* (2013.01); *A61K 31/438* (2013.01); *A61K 31/439* (2013.01); *A61K 31/4355* (2013.01); *A61K 31/44* (2013.01); *A61K 31/4402* (2013.01); *A61K 31/4433* (2013.01); *A61K 31/517* (2013.01); *A61K 31/52* (2013.01); *A61K 31/5377* (2013.01); *A61K 45/06* (2013.01); *G01N 33/53* (2013.01); *C12N 15/113* (2013.01); *C12N 2310/14* (2013.01); *C12N 2310/531* (2013.01); *G01N 2440/14* (2013.01); *G01N 2500/04* (2013.01)

(58) Field of Classification Search
None
See application file for complete search history.

(56) References Cited

FOREIGN PATENT DOCUMENTS

WO   WO 2011-062939   5/2011
WO   WO 2011-063309   5/2011

OTHER PUBLICATIONS

Wei and Xu (International Journal of Cancer, 2011, vol. 129, pp. 275-284).*
Yap et al (Current Opinion in Pharmacology, 2008, vol. 8, pp. 393-412).*
Mizuarai et al (Molecular Cancer, 2009, vol. 8, Issue 4, pp. 1-10).*
Katoh and Katoh, "Hedgehog signaling pathway and gastrointestinal stem cell signaling network (review)," *Int. J. Mol. Med.*, 18:1019-1023, 2006.
Katoh and Katoh, "Hedgehog target genes: mechanisms of carcinogenesis induced by aberrant hedgehog signaling activation," *Curr. Mol. Med.*, 9:873-886, 2009.
Katoh and Katoh, "Integrative genomic analyses on GLI1: positive regulation of GLI1 by Hedgehog-GLI, TGFbeta-Smads, and RTK-PI3K-AKT signals, and negative regulation of GLI1 by Notch-CSL-HES/HEY, and GPCR-Gs-PKA signals," *Int. J. Oncol.*, 35:187-192, 2009.
Lee et al., "Novel targets in esophageal and gastric cancer: beyond antiangiogenesis," *Expert Opin. Investig. Drugs*, 18:1351-1364, 2009.
PCT International Preliminary Report on Patentability issued in International Application No. PCT/US2013/021401, mailed Jul. 24, 2014.
PCT International Search Report and Written Opinion issued in International Application No. PCT/US2013/021401, mailed May 1, 2013.
Rizvi et al., "Combinatorial chemoprevention reveals a novel smoothened-independent role of GLI1 in esophageal carcinogenesis," *Cancer Research*, 70(17):6787-6796, 2010.
Scales and de Sauvage, "Mechanisms of Hedgehog pathway activation in cancer and implications for therapy," *Trends Pharmacol. Sci.*, 30:303-312, 2009.
Sheng et al., "Regulation of Gli1 localization by the cAMP/protein kinase A signaling axis through a site near the nuclear localization signal," *Journal of Biological Chemistry*, 281(1):9-12, 2006.
Stanton and Peng, "Small-molecule modulators of the Sonic Hedgehog signaling pathway," *Mol. Biosyst.*, 6:44-54, 2010.
Wang et al., "The crosstalk of mTOR/S6K1 and hedgehog pathways," *Cancer Cell*, 21(3):374-387, 2012.
Wiedmann and Caca, "Molecularly targeted therapy for gastrointestinal cancer," *Curr. Cancer Drug Targets*, 5:171-193, 2005.

* cited by examiner

*Primary Examiner* — Karen Canella
(74) *Attorney, Agent, or Firm* — Parker Highlander PLLC

(57) ABSTRACT

Methods and composition for tumor therapy, especially esophageal adenocarcinoma (EAC), are described. For example, in certain aspects methods for determining Hedgehog and mTOR signaling pathway status to select patients for administering a combination therapy of Hedgehog and mTOR signaling inhibitors are described. Furthermore, the invention provides compositions that involve testing kits for determining signaling status.

13 Claims, 23 Drawing Sheets

FIGS. 19A-C

SEQUENCE LISTING

```
<160> NUMBER OF SEQ ID NOS: 46

<210> SEQ ID NO 1
<211> LENGTH: 6
<212> TYPE: PRT
<213> ORGANISM: Homo sapiens

<400> SEQUENCE: 1

Lys Lys Arg Ala Leu Ser
1               5

<210> SEQ ID NO 2
<211> LENGTH: 6
<212> TYPE: PRT
<213> ORGANISM: Artificial Sequence
<220> FEATURE:
<223> OTHER INFORMATION: Consensus motif
<220> FEATURE:
<221> NAME/KEY: misc_feature
<222> LOCATION: (1)..(1)
<223> OTHER INFORMATION: Xaa is Lys or Arg
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa is Ser or Thr

<400> SEQUENCE: 2

Xaa Xaa Arg Xaa Xaa Xaa
1               5

<210> SEQ ID NO 3
<211> LENGTH: 19
<212> TYPE: DNA
<213> ORGANISM: Artificial Sequence
<220> FEATURE:
<223> OTHER INFORMATION: Synthetic primer

<400> SEQUENCE: 3
ctttgatcct tacctccca                                                  19

<210> SEQ ID NO 4
<211> LENGTH: 19
<212> TYPE: DNA
<213> ORGANISM: Artificial Sequence
```

```
<220> FEATURE:
<223> OTHER INFORMATION: Synthetic primer

<400> SEQUENCE: 4
agctccagtg aacacatat                                              19

<210> SEQ ID NO 5
<211> LENGTH: 19
<212> TYPE: DNA
<213> ORGANISM: Artificial Sequence
<220> FEATURE:
<223> OTHER INFORMATION: Synthetic primer

<400> SEQUENCE: 5
ctcgctagtg gcctacatc                                              19

<210> SEQ ID NO 6
<211> LENGTH: 19
<212> TYPE: DNA
<213> ORGANISM: Artificial Sequence
<220> FEATURE:
<223> OTHER INFORMATION: Synthetic primer

<400> SEQUENCE: 6
tgggactggc agcccatcc                                              19

<210> SEQ ID NO 7
<211> LENGTH: 19
<212> TYPE: DNA
<213> ORGANISM: Artificial Sequence
<220> FEATURE:
<223> OTHER INFORMATION: Synthetic primer

<400> SEQUENCE: 7
cggaaatcaa taggagttg                                              19

<210> SEQ ID NO 8
<211> LENGTH: 19
<212> TYPE: DNA
<213> ORGANISM: Artificial Sequence
<220> FEATURE:
<223> OTHER INFORMATION: Synthetic primer

<400> SEQUENCE: 8
cgaaggaaca acccttgtc                                              19

<210> SEQ ID NO 9
<211> LENGTH: 19
<212> TYPE: DNA
<213> ORGANISM: Artificial Sequence
<220> FEATURE:
<223> OTHER INFORMATION: Synthetic primer

<400> SEQUENCE: 9
cgtacgcgga atacaacga                                              19

<210> SEQ ID NO 10
<211> LENGTH: 20
<212> TYPE: DNA
<213> ORGANISM: Artificial Sequence
<220> FEATURE:
<223> OTHER INFORMATION: Synthetic primer

<400> SEQUENCE: 10
gcagaatcgc ctccggatcc                                             20
```

```
<210> SEQ ID NO 11
<211> LENGTH: 20
<212> TYPE: DNA
<213> ORGANISM: Artificial Sequence
<220> FEATURE:
<223> OTHER INFORMATION: Synthetic primer

<400> SEQUENCE: 11
acgtggagca gctcggcatc                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic primer

<400> SEQUENCE: 12
agaaggaggt cctgccgtcc                                               20

<210> SEQ ID NO 13
<211> LENGTH: 20
<212> TYPE: DNA
<213> ORGANISM: Artificial Sequence
<220> FEATURE:
<223> OTHER INFORMATION: Synthetic primer

<400> SEQUENCE: 13
ggtccaggta gttcatggcc                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
tcgagaccaa cgtggaggag                                               20

<210> SEQ ID NO 15
<211> LENGTH: 20
<212> TYPE: DNA
<213> ORGANISM: Artificial Sequence
<220> FEATURE:
<223> OTHER INFORMATION: Synthetic primer

<400> SEQUENCE: 15
ccgagtccag gtgttgtagg                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
ccagccagag agaccaacag                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic primer
```

```
<400> SEQUENCE: 17
gtgcggataa ccgtctgcag                                                20

<210> SEQ ID NO 18
<211> LENGTH: 18
<212> TYPE: DNA
<213> ORGANISM: Artificial Sequence
<220> FEATURE:
<223> OTHER INFORMATION: Synthetic primer

<400> SEQUENCE: 18
cgagcacaga gcctcgcc                                                  18

<210> SEQ ID NO 19
<211> LENGTH: 18
<212> TYPE: DNA
<213> ORGANISM: Artificial Sequence
<220> FEATURE:
<223> OTHER INFORMATION: Synthetic primer

<400> SEQUENCE: 19
gcgaagccgg ccttgcac                                                  18

<210> SEQ ID NO 20
<211> LENGTH: 20
<212> TYPE: PRT
<213> ORGANISM: Homo sapiens

<400> SEQUENCE: 20

Pro Arg Ser Ala Val Lys Leu Thr Lys Lys Arg Ala Leu Ser Ile Ser
1               5                   10                  15

Pro Leu Ser Asp
            20

<210> SEQ ID NO 21
<211> LENGTH: 20
<212> TYPE: PRT
<213> ORGANISM: Macaca mulatta

<400> SEQUENCE: 21

Pro Arg Ser Ala Val Lys Leu Thr Lys Lys Arg Ala Leu Ser Ile Ser
1               5                   10                  15

Pro Leu Ser Asp
            20

<210> SEQ ID NO 22
<211> LENGTH: 20
<212> TYPE: PRT
<213> ORGANISM: Bos taurus

<400> SEQUENCE: 22

Pro Arg Ser Ala Val Lys Leu Thr Lys Lys Arg Ala Leu Ser Ile Ser
1               5                   10                  15

Pro Leu Ser Asp
            20

<210> SEQ ID NO 23
<211> LENGTH: 20
<212> TYPE: PRT
<213> ORGANISM: Canis familiaris
```

```
<400> SEQUENCE: 23

Pro Arg Ser Ala Val Lys Leu Thr Lys Lys Arg Ala Leu Ser Ile Ser
1               5                   10                  15

Pro Leu Ser Asp
            20

<210> SEQ ID NO 24
<211> LENGTH: 20
<212> TYPE: PRT
<213> ORGANISM: Rattus norvegicus

<400> SEQUENCE: 24

Pro Arg Ser Ser Val Lys Leu Thr Lys Lys Arg Ala Leu Ser Ile Ser
1               5                   10                  15

Pro Leu Ser Asp
            20

<210> SEQ ID NO 25
<211> LENGTH: 20
<212> TYPE: PRT
<213> ORGANISM: Mus musculus

<400> SEQUENCE: 25

Pro Arg Ser Ser Val Lys Leu Thr Lys Lys Arg Ala Leu Ser Ile Ser
1               5                   10                  15

Pro Leu Ser Asp
            20

<210> SEQ ID NO 26
<211> LENGTH: 20
<212> TYPE: PRT
<213> ORGANISM: Gallus gallus

<400> SEQUENCE: 26

Pro Arg Gly Ala Gly Lys Leu Gly Lys Lys Arg Ala Leu Ser Ile Ser
1               5                   10                  15

Pro Leu Ser Asp
            20

<210> SEQ ID NO 27
<211> LENGTH: 20
<212> TYPE: PRT
<213> ORGANISM: Xenopus laevis

<400> SEQUENCE: 27

Pro Arg Ser Thr Met Leu Lys Ser Lys Lys Arg Ala Met Ser Ile Ser
1               5                   10                  15

Pro Leu Ser Asp
            20

<210> SEQ ID NO 28
<211> LENGTH: 20
<212> TYPE: PRT
<213> ORGANISM: Danio rerio

<400> SEQUENCE: 28

Pro Arg Ser Met Leu Lys Leu Ser Lys Lys Arg Ala Leu Ser Ile Ser
1               5                   10                  15

Pro Leu Ser Asp
            20
```

-continued

<210> SEQ ID NO 29
<211> LENGTH: 20
<212> TYPE: PRT
<213> ORGANISM: Drosophila melanogaster

<400> SEQUENCE: 29

Gly Ser Ile Arg Ala Ser Ile Ser Arg Lys Arg Ala Leu Ser Ser Ser
1               5                   10                  15

Pro Tyr Ser Asp
            20

<210> SEQ ID NO 30
<211> LENGTH: 15
<212> TYPE: PRT
<213> ORGANISM: Homo sapiens

<400> SEQUENCE: 30

Ser Pro Arg Val Arg Thr Leu Ser Gly Ser Arg Pro Pro Leu Leu
1               5                   10                  15

<210> SEQ ID NO 31
<211> LENGTH: 15
<212> TYPE: PRT
<213> ORGANISM: Homo sapiens

<400> SEQUENCE: 31

Arg Glu Arg Ser Arg Thr Gly Ser Glu Ser Ser Gln Thr Gly Thr
1               5                   10                  15

<210> SEQ ID NO 32
<211> LENGTH: 15
<212> TYPE: PRT
<213> ORGANISM: Homo sapiens

<400> SEQUENCE: 32

Gly Gly Arg Glu Arg Leu Ala Ser Thr Asn Asp Lys Gly Ser Met
1               5                   10                  15

<210> SEQ ID NO 33
<211> LENGTH: 15
<212> TYPE: PRT
<213> ORGANISM: Homo sapiens

<400> SEQUENCE: 33

Ser Gly Arg Pro Arg Thr Thr Ser Phe Ala Glu Ser Cys Lys Pro
1               5                   10                  15

<210> SEQ ID NO 34
<211> LENGTH: 15
<212> TYPE: PRT
<213> ORGANISM: Homo sapiens

<400> SEQUENCE: 34

Glu Phe Arg Pro Arg Ser Lys Ser Gln Ser Ser Ser Asn Cys Ser
1               5                   10                  15

<210> SEQ ID NO 35
<211> LENGTH: 15
<212> TYPE: PRT
<213> ORGANISM: Homo sapiens

<400> SEQUENCE: 35

Thr Arg Arg Ser Arg Thr Glu Ser Ile Thr Ala Thr Ser Pro Ala
1               5                   10                  15

```
<210> SEQ ID NO 36
<211> LENGTH: 15
<212> TYPE: PRT
<213> ORGANISM: Homo sapiens

<400> SEQUENCE: 36

Arg Phe Arg Lys Arg Thr His Ser Ala Gly Thr Ser Pro Thr Ile
1               5                   10                  15

<210> SEQ ID NO 37
<211> LENGTH: 15
<212> TYPE: PRT
<213> ORGANISM: Homo sapiens

<400> SEQUENCE: 37

Gly Cys Arg Arg Arg His Ser Ser Glu Thr Phe Ser Ser Thr Pro
1               5                   10                  15

<210> SEQ ID NO 38
<211> LENGTH: 15
<212> TYPE: PRT
<213> ORGANISM: Homo sapiens

<400> SEQUENCE: 38

Asn Lys Arg Ser Arg Thr Arg Thr Asp Ser Tyr Ser Ala Gly Gln
1               5                   10                  15

<210> SEQ ID NO 39
<211> LENGTH: 15
<212> TYPE: PRT
<213> ORGANISM: Homo sapiens

<400> SEQUENCE: 39

Arg Ser Arg Thr Arg Thr Asp Ser Tyr Ser Ala Gly Gln Ser Val
1               5                   10                  15

<210> SEQ ID NO 40
<211> LENGTH: 15
<212> TYPE: PRT
<213> ORGANISM: Homo sapiens

<400> SEQUENCE: 40

Pro His Lys Arg Arg Lys Thr Ser Asp Ala Asn Glu Thr Glu Asp
1               5                   10                  15

<210> SEQ ID NO 41
<211> LENGTH: 15
<212> TYPE: PRT
<213> ORGANISM: Homo sapiens

<400> SEQUENCE: 41

Leu Ser Arg Ser Arg Thr Ala Ser Leu Thr Ser Ala Ala Ser Val
1               5                   10                  15

<210> SEQ ID NO 42
<211> LENGTH: 15
<212> TYPE: PRT
<213> ORGANISM: Homo sapiens

<400> SEQUENCE: 42

Arg Ser Arg Ser Arg Thr Leu Ser Gln Ser Ser Glu Ser Gly Thr
1               5                   10                  15
```

```
<210> SEQ ID NO 43
<211> LENGTH: 15
<212> TYPE: PRT
<213> ORGANISM: Homo sapiens

<400> SEQUENCE: 43

Lys Arg Arg Leu Arg Lys Asn Ser Ser Arg Asp Ser Gly Arg Gly
1               5                   10                  15

<210> SEQ ID NO 44
<211> LENGTH: 15
<212> TYPE: PRT
<213> ORGANISM: Homo sapiens

<400> SEQUENCE: 44

Asn Arg Arg Ile Arg Thr Leu Thr Glu Pro Ser Val Asp Phe Asn
1               5                   10                  15

<210> SEQ ID NO 45
<211> LENGTH: 15
<212> TYPE: PRT
<213> ORGANISM: Homo sapiens

<400> SEQUENCE: 45

Ile Ala Lys Arg Arg Arg Leu Ser Ser Leu Arg Ala Ser Thr Ser
1               5                   10                  15

<210> SEQ ID NO 46
<211> LENGTH: 15
<212> TYPE: PRT
<213> ORGANISM: Homo sapiens

<400> SEQUENCE: 46

Ala Lys Arg Arg Arg Leu Ser Ser Leu Arg Ala Ser Thr Ser Lys
1               5                   10                  15
```

PERSONALIZED MEDICINE FOR THE PREDICTION OF THERAPY TARGETING THE HEDGEHOG PATHWAY

This application is a national phase application under 35 U.S.C. §371 of International Application No. PCT/US2013/021401, filed Jan. 14, 2013, which claims the benefit of U.S. Provisional Patent Application No. 61/585,872, filed Jan. 12, 2012, and 61/591,034, filed Jan. 26, 2012, each of which is incorporated herein by reference in its entirety.

BACKGROUND OF THE INVENTIONS

1. Field of the Invention

The present invention relates generally to the fields of oncology, molecular biology, cell biology, and cancer. More particularly, it concerns cancer classification using molecular markers and cancer therapy.

2. Description of Related Art

Esophageal adenocarcinoma (EAC) is one of the most aggressive cancers in the world, characterized by high mortality and poor prognosis (Jemal et al., 2009). In the U.S., EAC has increased at a frequency of 5%-10% per year since the 1980s, making it the fastest growing malignancy (Jemal et al., 2009). Despite multidisciplinary therapeutic approaches, EAC remains a virulent disease with an overall 5-year survival rate<20% (Hongo et al., 2009). It is very urgent to discover novel therapeutic targets for prevention and establish biomarkers useful for early detection of high-risk populations. Esophageal chronic inflammation induced by gastro-esophageal reflux disease is an important factor contributing to EAC (Lambert and Hainaut, 2007a; Lambert and Hainaut, 2007b), and some inflammation-related cytokines have been found to play pivotal roles in the development of EAC, especially tumor necrosis factor (TNF) α (Eksteen et al., 2001).

Hedgehog signaling plays a role in many stages of development, especially in formation of left-right symmetry. Loss or reduction of hedgehog signaling leads to multiple developmental deficits and malformations, one of the most striking of which is cyclopia. Many cancers and proliferative conditions have been shown to depend on the hedgehog pathway. The growth of such cells and survival can be affected by treatment with the compounds disclosed herein.

The need still exists for identifying new cancer therapies, in particular new uses for hedgehog inhibitors, alone or in combination with other therapeutic agents, for treatment of cancer, especially esophageal cancers that are resistant to hedgehog modulation.

SUMMARY OF THE INVENTION

Aspects of the present invention overcome a major deficiency in the art by providing novel methods and compositions for treating a tumor with personalized therapy. For example, there may be provided methods of treating a subject having a tumor or gastrointestinal tract disease or cancer, wherein the methods comprise obtaining information on mTOR (mammalian target of rapamycin) signaling (e.g., S6K phosphorylation or any known marker) and Hedgehog signaling (e.g., Gli1 expression or nuclear localization or any known marker) in a tumor or diseased sample of the subject. The method may further comprise administering to the subject a therapy based on the determined information.

For example, the method may comprise selecting a subject having an esophageal tumor or Barrett's esophagus and who has been determined to have elevated S6K phosphorylation (or Gli1 phosphorylation) relative to a first reference level and elevated Gli1 expression (or Gli1 nuclear localization) relative to a second reference level, and administering a therapy comprising an SMO inhibitor and mTOR inhibitor to the subject.

In alternative aspects, the method may comprise selecting a subject having an esophageal tumor or Barrett's esophagus and who has been determined to have elevated S6K phosphorylation (or Gli1 phosphorylation) relative to a first reference level but not elevated Gli1 expression (or Gli1 nuclear localization) relative to a second reference level, and administering a therapy comprising an mTOR inhibitor but not an SMO inhibitor.

In alternative aspects, the method may comprise selecting a subject having an esophageal tumor or Barrett's esophagus and who has been determined to have elevated Gli1 expression (or nuclear localization) but not elevated S6K phosphorylation (or Gli1 phosphorylation), and administering a therapy comprising an SMO inhibitor but not an mTOR inhibitor.

In certain aspects, the method may be defined as a method of selecting a subject having an esophageal tumor or Barrett's esophagus and who has been determined to have elevated S6K phosphorylation (or Gli1 phosphorylation) relative to a first reference level and elevated Gli1 expression (or Gli1 nuclear localization) relative to a second reference level, and administering a therapy comprising an SMO inhibitor and an mTOR inhibitor to the subject.

In further aspects, the method may be defined as a method of selecting a subject having an esophageal tumor or Barrett's esophagus and who has been determined to have elevated S6K phosphorylation (or Gli1 phosphorylation) relative to a first reference level but not elevated Gli1 expression (or Gli1 nuclear localization) relative to a second reference level, and administering a therapy comprising an mTOR inhibitor but not an SMO inhibitor.

In still further aspects, the method may be defined as a method of selecting a subject having an esophageal tumor or Barrett's esophagus and who has been determined to have elevated Gli1 expression (or nuclear localization) but not elevated S6K phosphorylation (or Gli1 phosphorylation), and administering a therapy comprising an SMO inhibitor but not an mTOR inhibitor. Any target-specific inhibitors used herein (e.g., SMO inhibitors, mTOR inhibitors, or AKT inhibitors) may include inhibitory molecules that directly or indirectly (for example, through at least or at most two, three, four, five or more mediators) inhibit the target's activity or reduce its expression.

For example, the SMO inhibitor may be any inhibitors that inhibit the Hedgehog pathway, such as GDC-0449, Cyclopamine, IPI-926, or BMS-833923 (XL139). In one embodiment, the SMO inhibitor is administered systemically, e.g., orally, subcutaneously, or intravenously.

mTOR inhibitors may include inhibitory molecules that directly or indirectly (for example, through at least or at most two, three, four, five or more mediators) inhibit mTOR activity or reduce its expression. Non-limiting examples of mTOR inhibitors may include rapamycin, temsirolimus (TORISEL®), everolimus (RAD001, AFINITOR®), ridaforolimus, AP23573, AZD8055, BEZ235, BGT226, XL765, PF-4691502, GDC0980, SF1 126, OSI-027, GSK1059615, KU-0063794, WYE-354, INK128, temsirolimus (CCI-779), Palomid 529 (P529), PF-04691502, or PKI-587. In one embodiment, the mTOR inhibitor inhibits TORC1 and TORC2. Examples of TORC1 and TORC2 dual inhibitors include, e.g., OSI-027, XL765, Palomid 529, and INK128.

Particular examples of mTOR inhibitors may be Rapamycin, WYE354, RAD001, and AP23573.

The mTOR inhibitors may also include S6K1 (p70 ribosomal S6 kinase 1) inhibitors, AKT inhibitors, ERK (extracellular signal-regulated kinase) inhibitors, or IKKβ inhibitors. AKT inhibitors may be an inhibitor of AKT-1, AKT-2, and/or AKT-3. Examples of AKT inhibitors may include Triciribine (TCN), also known as Akt/PKB inhibitor-2 (API-2), or Triciribine phosphate (TCNP) or MK2206. ERK inhibitors include any ERK inhibitors known in the art, such as AZD6244. IKKβ inhibitors include any IKKβ inhibitors known in the art, such as BAY11-7082.

In one embodiment, the mTOR inhibitor is administered systemically, e.g., orally, subcutaneously, or intravenously. The mTOR inhibitor can be administered via the same or a different route than the SMO inhibitor.

There may be provided a method for determining a subject's response to an SMO inhibitor therapy or mTOR inhibitor therapy. The method may comprise testing a tumor sample or a diseased sample of a subject to determine S6K phosphorylation (or Gli1 phosphorylation) and Gli1 expression (or nuclear localization), wherein if the subject has elevated S6K phosphorylation (or Gli1 phosphorylation) relative to a first reference level and elevated Gli1 expression (or Gli1 nuclear localization) relative to a second reference level, the subject is more likely to have resistance to an SMO inhibitor therapy alone and favorable response to a therapy comprising an SMO inhibitor and a mTOR inhibitor; if the subject has elevated S6K phosphorylation (or Gli1 phosphorylation) relative to a first reference level but not elevated Gli1 expression (or Gli1 nuclear localization) relative to a second reference level, the subject is more likely to have a favorable response to a therapy comprising an mTOR inhibitor but not an SMO inhibitor; or if the subject has elevated Gli1 expression (or Gli1 nuclear localization) relative to a first reference level but not elevated S6K phosphorylation (or Gli1 phosphorylation) relative to a second reference level, the subject is more likely to have a favorable response to a therapy comprising an SMO inhibitor but not an mTOR inhibitor.

Determining whether the sample exhibits elevated phosphorylation, expression, or nuclear localization can be by any method known to those of ordinary skill in the art, such as protein analysis as carried out by immunohistochemistry (IHC) or Western blot analysis. Techniques that may be involved in this determination are well known to those of ordinary skill in the art. Gli expression may be determined by either protein quantification or nucleotide analysis of Gli mRNA. Examples of quantifying Gli1 mRNA include nucleic hybridization or RT-PCR.

There may also be provided a method of treating Barrett's esophagus (BE), comprising administering a therapy comprising an SMO inhibitor and a mTOR inhibitor to a subject having Barrett's esophagus. The method may be further defined as selecting a subject having Barrett's esophagus and who has been determined to have elevated S6K phosphorylation (or Gli1 phosphorylation) relative to a first reference level and elevated Gli1 expression (or Gli1 nuclear localization) relative to a second reference level, and administering a therapy comprising an SMO inhibitor and mTOR inhibitor to the subject.

Certain aspects of the present invention also contemplate the preparation of kits or arrays for use in accordance with the present invention. Suitable kits include various reagents for use in accordance with the present invention in suitable containers and packaging materials, including tubes, vials, and shrink-wrapped and blow-molded packages. Such an array or a kit may comprise a first antibody that recognizes S6K phosphorylation or a second antibody that recognizes Gli1 phosphorylation, and a third antibody that binds Gli1 or a nucleotide that binds Gli1 mRNA. The array may be a tissue microarray. The array may be a protein or DNA chip or a combination thereof. There may be permutations of the reagents in the kit or array. For example, the array or kit may comprise the first antibody and the third antibody aliquoted in separate containers, the first antibody and the nucleotide aliquoted in separate containers, the second antibody and the third antibody aliquoted in separate containers, or the second antibody and the nucleotide aliquoted in separate containers.

By "subject" or "patient" is meant any single subject for which therapy is desired, including humans, cattle, dogs, guinea pigs, rabbits, chickens, and so on. Also intended to be included as a subject are any subjects involved in clinical research trials not showing any clinical sign of disease, or subjects involved in epidemiological studies, or subjects used as controls.

As used herein, "elevated expression, phosphorylation, or nuclear localization" refers to an elevated or increased level of expression, phosphorylation, or nuclear localization in a tumor or diseased sample relative to a suitable reference level in a suitable control (e.g., a non-cancerous or non-diseased tissue or cell sample, or a reference standard), wherein the elevation or increase is statistically-significant ($p<0.05$). Whether an increase in the expression, phosphorylation, or nuclear localization of a protein in a cancer sample relative to a control is statistically significant can be determined using an appropriate t-test (e.g., one-sample t-test, two-sample t-test, Welch's t-test) or other statistical test known to those of skill in the art.

As used herein, "decreased expression, phosphorylation, or nuclear localization" refers to a reduced or decreased level of expression, phosphorylation, or nuclear localization in a tumor or diseased sample relative to a suitable reference level in a suitable control (e.g., a non-cancerous or non-diseased tissue or cell sample, or a reference standard), wherein the reduction or decrease in the level of gene expression is statistically significant ($p<0.05$). In some embodiments, the reduced or decreased level of gene expression can be a complete absence of gene expression, or an expression level of zero. Whether a decrease in the expression, phosphorylation, or nuclear localization of a protein in a cancer sample relative to a control is statistically significant can be determined using an appropriate t-test (e.g., one-sample t-test, two-sample t-test, Welch's t-test) or other statistical test known to those of skill in the art.

The control may comprise data obtained at the same time (e.g., in the same hybridization experiment) as the patient's individual data, or may be a stored value or set of values, e.g., stored on a computer or on computer-readable media. If the latter is used, new patient data for the selected marker(s), obtained from initial or follow-up samples, can be compared to the stored data for the same marker(s) without the need for additional control experiments.

Embodiments discussed in the context of methods and/or compositions of the invention may be employed with respect to any other method or composition described herein. Thus, an embodiment pertaining to one method or composition may be applied to other methods and compositions of the invention as well.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following figures form part of the present specification and are included to further demonstrate certain aspects of the invention. The invention may be better understood by reference to one or more of these drawings in combination with the detailed description of specific embodiments presented herein.

FIG. 1A. Luciferase assay for Gli transcriptional activity in esophageal adenocarcinoma (EAC) cell lines with or without TNFα (5 ng/mL) stimulation. The EAC cells were transfected using GliBS-Luciferase or mGliBS-Luciferase with CMV-Renilla at a 10:1 ratio, serum-starved overnight, and then treated with TNFα for 24 hr. GliBS is a Gli-responsive reporter, and mGliBS is a Gli-unresponsive reporter. Error bars represent SD (n=5). FIG. 1B. The mRNA levels of Gli1 target genes in the EAC cell lines with or without TNFα (5 ng/mL) stimulation were examined by real-time PCR and normalized to the mRNA level of ACTIN. Error bars represent SD (n=4). FIG. 1C. EAC cells were co-treated with TNFα (5 ng/mL) and cyclopamine (Cyc, 0.5, 1, and 5 µM) or TNFα (5 ng/mL) and rapamycin (Rapa, 10, 50, and 100 nM) for 24 hr and then subjected to luciferase assay. Error bars represent SD (n=5 for cyclopamine treatment and 4 for rapamycin treatment). FIG. 1D. BE3 cells were treated with TNFα (5 ng/mL) alone (top panel) or co-treated with TNFα and rapamycin (50 nM, middle panel) or cyclopamine (1 µM, bottom panel) for the indicated time course. Then, the cells were lysed for cell fractionation followed by Western blotting. Lamin B and tubulin were used as markers for the nucleus and the cytoplasm, respectively. FIG. 1E. Immunofluorescent analysis of Gli1 in BE3 cells treated with TNFα (5 ng/mL) alone or co-treated with TNFα and rapamycin (50 nM) for the indicated time course. Scale bar=100 µm for original picture and 25 µm for inset. Dapi was used to stain nuclei.

FIG. 2A. BE3 or SKGT4 cells were treated with TNFα (5 ng/mL) alone or co-treated with TNFα and rapamycin (50 nM) for 6 hours, and then the cells were lysed and subjected to IP-Western blot assay to examine the interactions between mTOR pathway components with Gli1. FIG. 2B. BE3 cells were transiently transfected with HA-tagged wild-type S6K1 (HA-S6K1), constitutively activated S6K1T389E (HA-T389E), function-loss S6K1T389A (HA-T389A), or empty vector (EV). After 24 hour of the transfection, the cells were treated with or without rapamycin (100 nM) for an additional 6 hours followed by lysis and IP-Western assay to test the interaction between S6K1 variants and Gli1. Phosphorylated S6 (p-S6) was used as a marker for S6K1 activation. FIG. 2C. BE3 cells were transiently transfected with Gli-firefly and CMV-renilla reporters in combination with HA-S6K1, HA-T389E, HA-T389A, or EV. After 24 hour of the transfection, the cells were treated with or without rapamycin (100 nM) for an additional 24 hours followed by luciferase assay to measure the expression of the Gli reporter. Error bars represent SD (n=3). FIG. 2D. The mRNA levels of Gli1 target genes in the BE3 cells transiently transfected with HA-S6K1, HA-T389E, HA-T389A, or EV followed by treatment with or without rapamycin (100 nM) measured via real-time PCR. The mRNA levels of Gli1 target genes were normalized to the mRNA level of ACTIN. Error bars represent SD (n=3). FIG. 2E. Western blot analysis using the EAC cells transfected with control siRNA (Ctrl) or siRNA targeting S6K1 followed by TNFα treatment. FIG. 2F. EAC cells were transiently transfected with control siRNA (Ctrl) or siRNA targeting S6K1. After 48 hour of the transfection, the cells were further transfected with Gli-firefly and CMV-renilla reporters with or without TNFα for an additional 24 hours followed by luciferase assay. Error bars represent SD (n=3). FIG. 2G. BE3 cells were transiently transfected with control siRNA (Ctrl) or siRNA targeting S6K1 followed by treatment with TNFα or only treated with TNFα. The mRNA levels of Gli1 target genes in these cells were measured through real-time PCR and normalized to the mRNA level of ACTIN. Error bars represent SD (n=3).

FIG. 3A. The empty vector, wild-type S6K1, S6K1T389E, S6K1T389A, or kinase-dead S6K1 (S6K1K100R) were introduced into the BE3 cells, and endogenous Gli1 was immunoprecipitated for Western blot analysis. The phosphorylation was examined using anti-phospho-serine/threonine antibody. FIG. 3B. In vitro kinase assay using purified Gli1 fragment, containing 1-500 amino acids (Gli1F1), or Gli1F2, containing amino acid 501 to the end, plus purified wild-type S6K1 kinase or kinase-dead S6K1 (S6K1KD). Arrowheads 1 and 4 show phosphorylated Gli1F1 detected using anti-phospho-serine/threonine antibody; arrowheads 2 and 5 are purified Gli1F1 protein; arrowhead 3 is purified Gli1F2 protein. The phosphorylation of S6 acts as a positive control. FIG. 3C. The S6K1 recognizing motif in Gli1 from fruit fly to human (SEQ ID NOs: 20-29). FIG. 3D. In vitro kinase assay using purified Gli1F1 or Gli1F1 with the alanine substitution of serine 84 (S84A) plus purified S6K1. FIG. 3E. With the absence or presence of rapamycin (100 nM), BE3 cells were transiently transfected with S6K1 expression plasmid or treated with TNFα (5 ng/mL). The phosphorylation of Gli1S84 was detected using a phosphor-Gli1S84-specific antibody in Western blot analysis. FIG. 3F. BE3 cells were treated with TNFα (5 ng/mL) for 6 hours, and then, the cells were lysed for cell fractionation and subsequent Western blot analysis. The phosphorylation of Gli1S84 was detected using a phosphor-Gli1S84 specific antibody. Lamin B and tubulin were used as markers for the nucleus and the cytoplasm, respectively. FIG. 3G. BE3 cells were treated with TNFα alone, or TNFα plus siRNA targeting S6K1 mRNA 3' UTR with or without transfection of S6K1 expression plasmid, and then, the cells were lysed for Western blot analysis. FIG. 3H. Western blot analysis of BE3 cells transfected with control siRNA, or siRNA targeting mTOR, raptor, and rictor.

FIG. 4A. The BE3 stable clones with Gli1 knock-down. C: non-silencing control shRNA; #1-5: 5 different Gli1 shRNAs. FIG. 4B. The mRNA levels of Gli1 target genes in the BE3 stable clones with Gli1 knock-down measured via real-time PCR and normalized to the mRNA level of ACTIN. Error bars represent SD (n=3). FIG. 4C. Cell counting analysis of the BE3 stable clones with Gli1 knock-down. All cells were counted, and then $1 \times 10^5$ cells were seeded in 10-cm dishes. Error bars represent SD (n=3). FIG. 4D. MTT assay of the BE3 stable clones with Gli1 knock-down. All cells were counted, and then 3,000 cells were seeded in each well of a 96-well plate. Error bars represent SD (n=3).

FIG. 5A. Gli1 protein levels and Gli reporter activity in BE3 parental cells and the stable clones established from BE3 parental cells. EV: empty vector; S84A: alanine mutant of Gli1 Ser84; S84E: glutamine mutant of Gli1 Ser84. Error bars represent SD (n=3). FIG. 5B. The mRNA levels of the Gli1 target genes in BE3 parental cells and stable clones were examined through real-time PCR and normalized to the level of ACTIN. Error bars represent SD (n=3). FIG. 5C. Immunofluorescent analysis of Gli1 in the BE3 stable clones. Scale bar=100 μm for original picture and 25 μm for inset. Dapi was used to stain nuclei. FIG. 5D. In vivo tumorigenesis assay of the stable clones in nude mice. One million BE3 stable cells were subcutaneously injected into the right flank of nude mice, and tumor volume was measured and calculated using the formula: $l \times w^2$, where l is the longest diameter and w is the shortest diameter. Error bars represent SD (n=5). FIG. 5E. Interactions between Gli1 and SuFu in the stable clones through IP-Western analysis. FIG. 5F. Endogenous interactions between Gli1 and SuFu in BE3 cells with the treatment of TNFα (5 ng/mL) or ectopic expression of S6K1 with or without rapamycin (50 nM).

FIG. 6A. Statistic analysis of immunohistochemistry (IHC) staining of Gli1 and p-S6K1 from human EAC tissues. FIG. 6B. Representative IHC staining results for Gli1 and p-S6K1 in human EAC tissues. FIG. 6C. Statistic analysis for Gli1 and p-S6K1 correlation from the IHC staining results in human EAC tissues. FIG. 6D. Representative IHC staining results for p-Gli1 or p-S6K1 in human EAC tissue microarray. FIG. 6E. Statistical analysis for Gli1 and p-S6K1 correlation from the IHC staining results in human EAC tissue microarray. FIG. 6F. Statistic analysis for p-Gli1 and p-S6K1 correlation from the IHC staining results in human EAC tissue microarray. FIG. 6G. Statistic analysis for p-Gli1 and p-S6K1 correlation in the Gli1 positive subpopulation of human EAC tissue microarray.

FIG. 7A. The expression of activated SHH (SHH-N) in EAC cell lines and the cell culture medium. FIG. 7B. The mRNA levels of Gli1 target genes in EAC cell lines with or without SHH treatment (1 μg/mL). The mRNA levels of Gli1 target genes are normalized to ACTIN. Error bars represent SD (n=3). FIG. 7C. $IC_{50}$ of cyclopamine (top two panels) or GDC-0449 (bottom two panels) for the Gli1 stable clones. Error bars represent SD (n=4). FIG. 7D. $IC_{50}$ of cyclopamine (top two panels) or GDC-0449 (bottom two panels) for the Gli1 stable clones with existence of TNFα (5 ng/mL). Error bars represent SD (n=4). FIG. 7E. $IC_{50}$ of cyclopamine (top two panels) or GDC-0449 (bottom two panels) for EAC cells pre-treated with rapamycin (Rapa, 10 nM). Error bars represent SD (n=4). FIG. 7F. $IC_{50}$ of cyclopamine (top two panels) or GDC-0449 (bottom two panels) for the Gli1 stable clones with rapamycin (Rapa, 50 nM) treatment. Error bars represent SD (n=4). FIG. 7G. In vivo combination therapy for subcutaneously inoculated tumors from BE3 cells using GDC-0449 (50 mg/kg) or RAD001 (10 mg/kg). One million cells were subcutaneously injected into the right flank of nude mice and the tumor cells were allowed to grow for 10 days (the arrow) before initiation of drug treatment. The vehicle, GDC-0449, RAD001, or combination of GDC-0449 and RAD001 were orally administrated, qd. The tumor volume measured and calculated using the formula: $l \times w^2$, where l is the longest diameter and w is the shortest diameter. Error bars represent SD (n=5).

FIG. 8A. The regulation of S6K1 and Gli1 by ectopically expressed AKT or ERK in Hela cells with or without rapamycin (50 nM). FIG. 8B. The influence of S6K1 knock-down on the AKT or ERK-stimulated HH pathway in Hela cells. Error bars represent SD (n=3). FIG. 8C. Schematic diagram for the canonical HH pathway stimulated by HH ligands and SMO-independent Gli1 activation stimulated by the mTOR/S6K1 pathway including the drug targets, marked by "—", is shown.

FIG. 9A. Luciferase assay for Gli reporter using esophageal adenocarcinoma (EAC) cell lines with or without treatment of cyclopamine, GDC-0449, recombinant human sonic hedgehog (rhSHH), or TNFα. Error bars represent SD (n=4). FIG. 9B. Western blot analysis and luciferase assay for Gli reporter using EAC cell lines with or without transfection of scrambled siRNA as control (Ctrl), or two individual siRNA targeting SMO. Error bars represent SD (n=3). FIG. 9C. Western blot analysis and luciferase assay for Gli reporter using EAC cell lines with or without treatment of TNFα alone or in combination with WYE-354 (an mTOR ATP competitive inhibitors at concentrations of 10, 20, and 40 nM). Error bars represent SD (n=3). FIG. 9D. Western blot analysis using BE3 cells transfected with wild-type mTOR or rapamycin-resistant mTOR (mTORS2035T) followed by treatment of TNFα alone or in combination with rapamycin (50 nM). FIG. 9E. Luciferase assay for Gli reporter using BE3 cells transfected with wild-type mTOR or rapamycin-resistant mTOR (mTORS2035T) followed by treatment of TNFα alone or in combination with rapamycin (50 nM). Error bars represent SD (n=4). FIG. 9F. Western blot analysis and luciferase assay for Gli reporter using EAC cell lines transfected with or without transfection of control siRNA or siRNA targeting Gli1, Gli2, or Gli3, followed by TNFα treatment. Error bars represent SD (n=3). FIG. 9G. Immunofluorescent analysis of Gli1 in BE3 cells treated with TNFα (5 ng/mL) alone or co-treated with TNFα and rapamycin (50 nM) for indicated time course. Scale bar=100 μm for original picture and 25 μm for inset. Dapi was used to stain nuclei. FIG. 9H. Negative control for Gli1 immunofluorescence staining using normal rabbit IgG or secondary antibody only.

FIGS. 10A-10D. BE3 or SKGT4 cells were treated with TNFα (5 ng/mL) alone or plus rapamycin (50 nM) for 6 hr, and then the cells were lysed for IP-Western assay. FIG. 10E. Western blot analysis and FIG. 10F. Luciferase assay for Gli reporter using EAC cell lines with or without transfection of siRNA targeting S6K1 followed by TNFα treatment alone or TNFα plus ectopic expression of S6K1 variants. Error bars represent SD (n=4).

FIG. 11A. Recognition motif of well-known S6K1 substrates (SEQ ID NOs: 30-46 and the consensus motif of SEQ ID NO: 2). FIG. 11B. Mass spectrometric analysis of TNFα (5 ng/mL)-stimulated phosphorylation of endogenous Gli1 Ser84 in BE3 cells. Overnight serum-starved BE3 cells were treated with TNFα for 6 hr directly or following rapamycin pretreatment for 2 hr. Cells were then harvested for protein extraction, and endogenous Gli1 was immunoprecipitated from the cell lysate for mass spectrometric analysis. FIG. 11C. The antibody specificity for phosphorylated Gli1S84 was tested via IP-Western analysis. The BE3 cells were transfected with flag-tagged wild-type Gli1 (flag-Gli1WT) or Gli1 with substitution of serine 84 by alanine (flag-Gli1S84A), followed by treatment of TNFα alone or TNFα with rapamycin. FIG. 11D. Western blot analysis using EAC cell lines transfected with control siRNA or siRNA targeting Gli1 followed by TNFα treatment. FIG. 11E. The EAC cells were transfected with control siRNA or siRNA targeting Gli1 for 24 hr. Then the cells were counted and seeded in culture dishes for MTT and cell counting assays, or seeded on matrigel-covered transwells for invasion assays, followed by TNFα treatment. Error bars represent SD (n=3). FIG. 11F. The EAC cells were transfected with control siRNA or siRNA targeting Gli1 for 24 hr followed by S6K1 transfection for an additional 24 hr. Then, the cells were counted and seeded in culture dishes for MTT and cell counting assays, or seeded on matrigel-covered transwells for invasion assays. Error bars represent SD (n=3). FIG. 11G. Western blot analysis using the MEF cells with TSC2 knock-out (TSC2$^{-/-}$) and paired TSC2$^{+/+}$ MEF cells. FIG. 11H. Western blot analysis using BE3 cells with overnight serum-starvation followed by amino acid stimulation. FIG. 11I. Luciferase assay for Gli reporter using BE3 cells with knock-down of mTOR raptor, or rictor. Error bars represent SD (n=3).

FIG. 13A. Luciferase assay of Gli reporter in the stable clones treated by TNFα alone (5 ng/mL) or TNFα plus rapamycin (100 nM). Error bars represent SD (n=3). FIG. 13B. Gli1 immunofluorescence staining in several BE3 stable clones with TNFα treatment. Scale bar=100 µm for original picture and 25 µm for inset. FIG. 13C. The regulation of p-Gli1 by TNFα alone or together with rapamycin (10, 50, and 100 nM) in the BE3 stable clone. FIG. 13D. MTT assay of the various Gli1 stable clones. All cells were counted, and then 3,000 cells were seeded in each well of a 96-well plate. Error bars represent SD (n=3). FIG. 13E. Soft-agar assay of the various Gli1 stable clones. All cells were counted, and then 1,000 cells were mixed with agarose for each well of a 24-well plate. Left, representative microscopic images. Right, quantitation of colony formation. Error bars represent SD (n=3). FIG. 13F. Invasion assay of the various Gli1 stable clones. All cells were counted, and then 1,000 cells were seeded on matrigel in transwells. Left, representative microscopic images from the bottom side of transwell membranes. Right, quantitation of invasive cells. Error bars represent SD (n=3). FIGS. 13G-13I. The assays of MTT (G), soft agar (H), and invasion (I) using the BE3 stable clones treated with TNFα. Error bars represent SD (n=4 for G, n=3 for H and I). FIG. 13J. Images of tumorigenesis of the BE3 stable clones in nude mice through subcutaneous injection at the last time point. FIG. 13K. Interaction between Gli1WT, Gli1S84A, or Gli1S84E and SuFu in BE3 cells. Flag-tagged Gli1WT, Gli1S84A, or Gli1S84E was transfected into BE3 cells followed by IP-Western assay.

FIG. 14A. Immunohistochemistry analysis of Gli1, p-S6K1, or p-Gli1 in normal mouse colon tissues. FIGS. 14B-14C. Western blot analysis of Gli1 antibody used for IHC from EAC cells in (FIG. 14B) or BE3 cells with Gli1 knock-down in (FIG. 14C). FIG. 14D. IHC of Gli1 in EAC tissues with or without Gli1 peptides. FIG. 14E. Statistical analysis of IHC of Gli1 and p-S6K1 in rat EAC tissues. FIG. 14F. Immunohistochemistry analysis of p-Gli1 S84 antibody with or without Gli1 peptide used previously for developing this antibody or the matched non-phosphorylated Gli1 peptide. FIG. 14G. Statistical analysis of immunohistochemistry of p-Gli1 and p-S6K1 from human EAC tissue microarray. FIG. 14H. Representative images of Gli1 and p-S6K1 immunostaining in human tissue microarray of multiple cancers. FIG. 14I. Statistical analysis of immunohistochemistry of the Gli1 and p-S6K1 from human tissue microarray of multiple cancers.

FIG. 15A. The EAC cell lines were transfected with Gli-Luciferase and CMV-Renilla reporters followed by treatment with activated recombinant human SHH ligand (1 µg/mL) for 24 hr. Then, the luciferase assay was performed to measure the expression of Gli reporter in all tested EAC cell lines. Error bars represent SD (n=3). FIG. 15B. Western blot analysis and MTT assay using BE3 cells with or without TNFα alone or in combination with rapamycin. Error bars represent SD (n=3). FIG. 15C. EAC cells were transfected with control siRNA or siRNA targeting SMO for 48 hours. Then the cells were seeded for MTT assays with or without treatment of rapamycin (10 nM).

Figure 19:
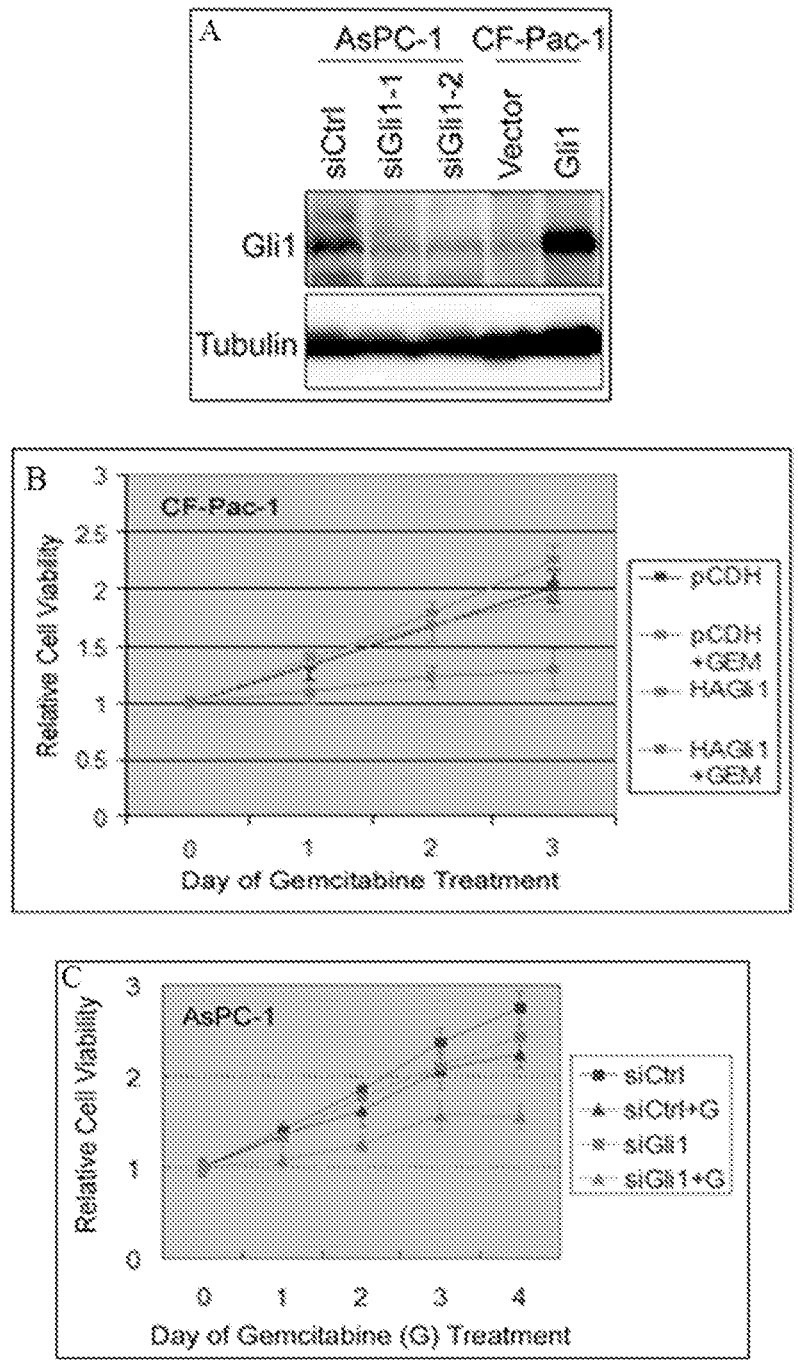

FIGS. 19A-C. Gli1 is negatively correlated with sensitivity of pancreatic cancer cells to GEM. Gli1 knock-down sensitized the response of PDAC cells to gemcitabine (GEM), but overexpression of Gli1 protected PDAC cells from GEM. FIG. 19A. Western blot of Gli1 in stable clones of AsPC-1 and CF-Pac-1 cells with Gli1 knocked down or ectopic expression. FIG. 19B. MTT assay of CF-Pac-1 stable clones with GEM. FIG. 19C. MTT assay of AsPC-1 stable clones with GEM.

Figure 20:
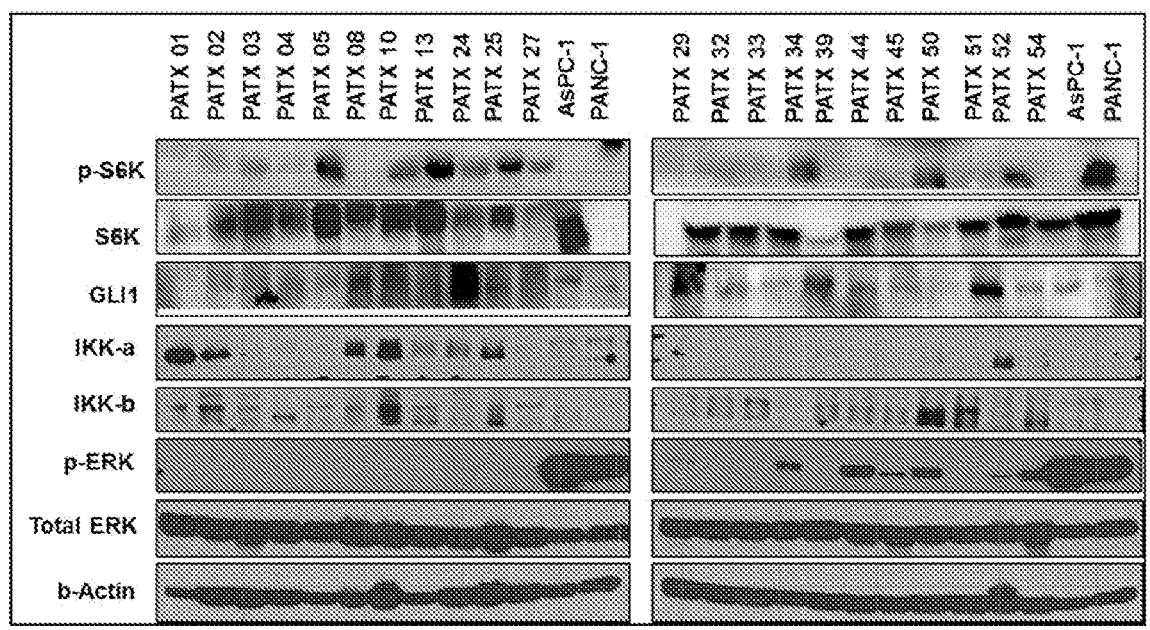

FIG. 20. The expression of kinases potentially regulates Gli1 in human PDAC xenograft from mouse (HIM) model. Human PAC xenografts show different kinase patterns. Gli1 might be regulated by different pathways in tumor tissues from different patients. Western blot of S6K1, phosphorylated S6K1, Gli1, IKK-alpha, IKK-beta, ERK, phosphorylated ERK, and beta-actin.

Figure 21:
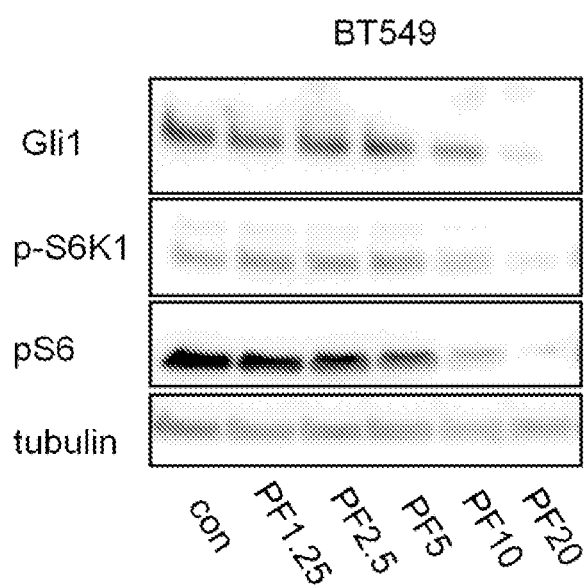

FIG. 21. Gli1 expression is decreased with the treatment of PF-4708671, a S6K1 inhibitor, indicating that Gli1 is also correlated with S6K1 in breast cancer cell lines. Western blot showing the effect of PF-4708671 on S6 phosphorylation, S6K1 phosphorylation, and Gli1 expression in the BT549 cell line. Tubulin was detected as a loading control. Lane labels indicate the micromolar concentration of PF-4708671 used.

Figure 22:
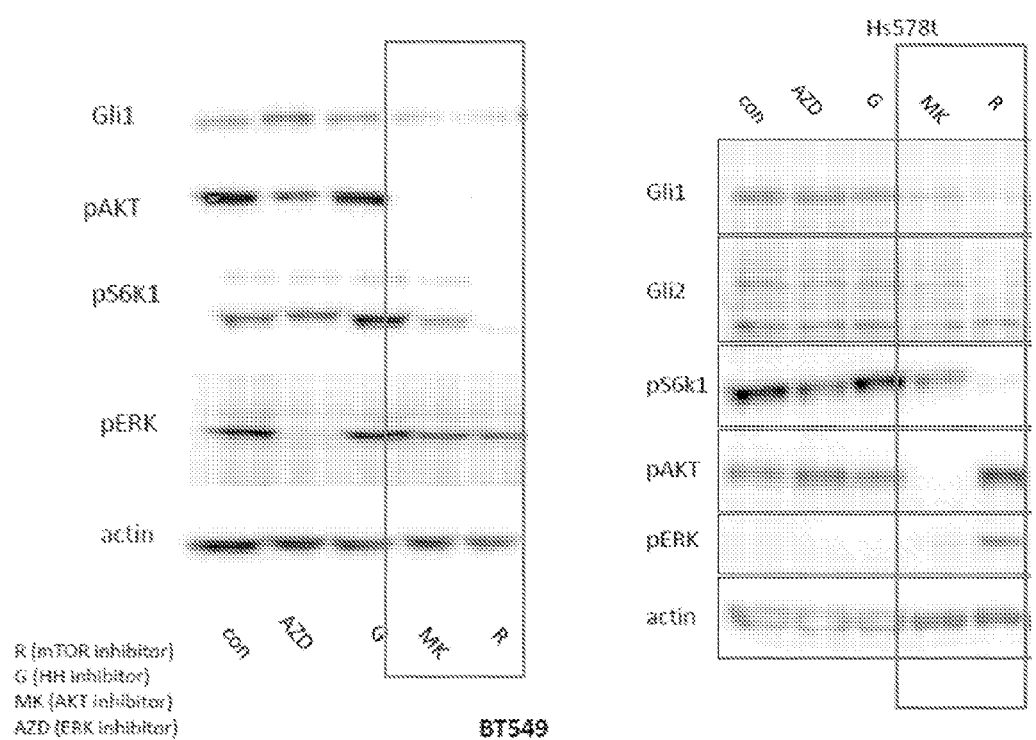

FIG. 22. AKT inhibitor (MK) and mTOR inhibitor (R), which inhibits S6K1 activation, decreased Gli1 protein levels in BT549 and Hs578t breast cancer cells (see black boxes). Western blot of Gli1, phosphorylated AKT, phosphorylated S6K1, phosphorylated ERK, and actin in BT549 and Hs578t cells after treatment with an mTOR inhibitor (R), an AKT inhibitor (MK), an HH inhibitor (G), or an ERK inhibitor (AZD). DMSO was used as a negative control.

Figure 23:
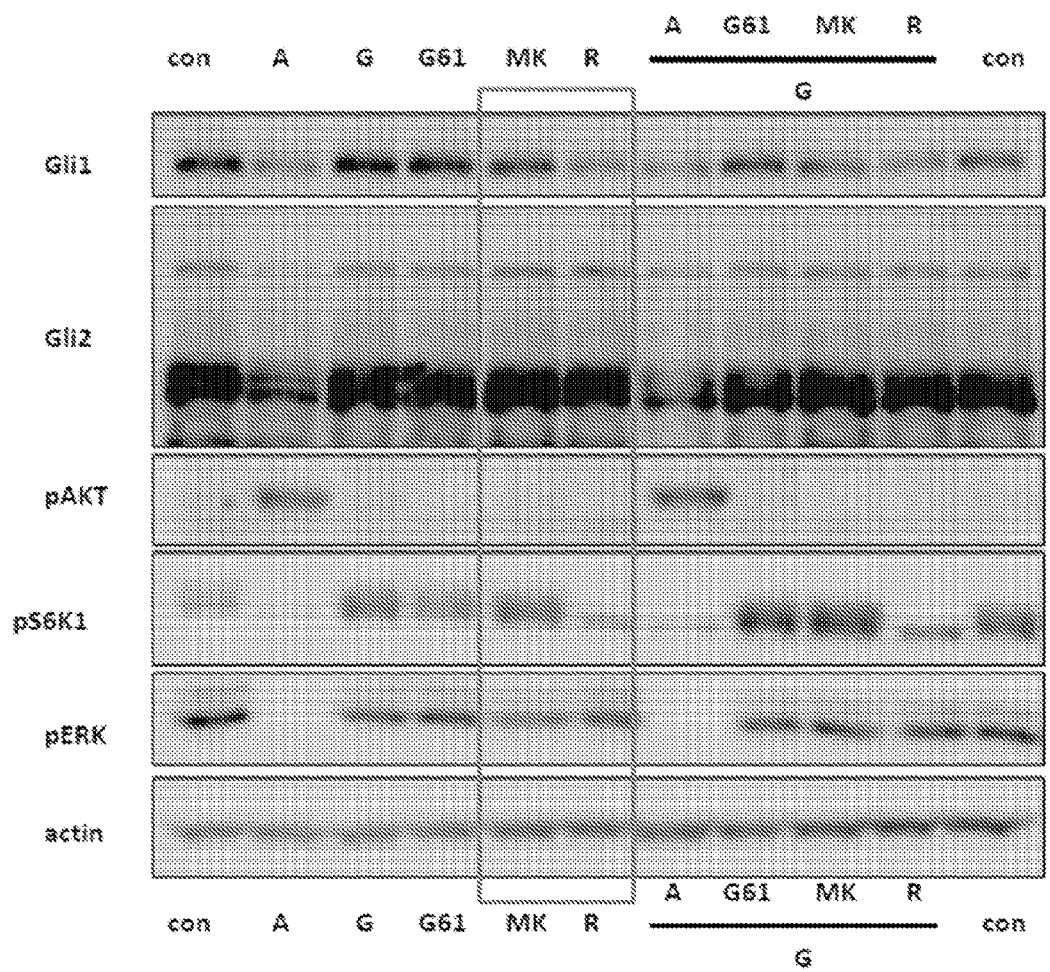

FIG. 23. AKT inhibitors and mTOR inhibitors, which inhibit S6K1 activation, decreased Gli1 protein levels in MDA-MB-231 breast cancer cells (see black box). A; AZD, ERK inhibitor; G: GDC-0449, HH inhibitor; G61: GANT61, Gli inhibitor; MK: MK2206, AKT inhibitor; R: RAD001, mTOR inhibitor; con: DMSO control.

Figure 24:
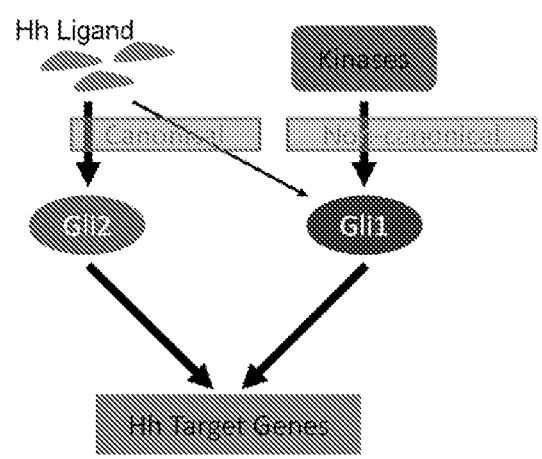

FIG. 24. Model showing that Gli1 is a marker for non-canonical HH pathway and Gli1 is a marker for canonical HH pathway.

DETAILED DESCRIPTION OF THE EMBODIMENTS

The present invention is directed to novel compositions and methods for treating tumors or a gastrointestinal tract disease, especially for treating subjects having an EAC or BE that may be resistant to Hedgehog pathway signaling inhibitors. Certain aspects of the invention provide novel compositions comprising inhibitors of two signaling pathways, Hedgehog pathway (SMO) and mTOR pathway, which may be combined with selection of patients based on relevant information.

The Hedgehog pathway plays crucial roles in many types of cancers, and several agents targeting SMO, the key mediator of canonical hedgehog pathway, are being tested in clinical trials for cancer therapy. Although these chemicals have shown potential efficacy, development of resistance has also been observed. It is demonstrated herein that mTOR/S6K1 directly activates Gli1 independent of SMO, which results in the resistance of tumor cells to inhibitors targeting SMO. However, mTOR inhibitors could enhance the inhibitory effects of SMO inhibitors on the tumor cells. Therefore, embodiments of the invention allow for the combined use of inhibitors against mTOR/S6K1 and Hedgehog pathways to achieve more effective cancer target therapy.

Previous work has shown that TNFα activates the mTOR pathway through IKKβ to stimulate the development and progression of EAC (Yen et al., 2008). The mechanistic target of rapamycin (mTOR) is a serine/threonine protein kinase, and its activation leads to the phosphorylation of S6K1 and 4E-BP1 (Guertin and Sabatini, 2007). S6K1 is also a serine/threonine kinase, and its phosphorylation by mTOR activates its function to promote the mRNA translation of target genes (Guertin and Sabatini, 2007). For 4E-BP1, however, phosphorylation by mTOR inactivates its function and de-represses its inhibition on cap-dependent translation (Guertin and Sabatini, 2007). The mTOR pathway has been established pivotally to be involved in many aspects of molecular and cellular biology, including mRNA translation, ribosome biogenesis, cell growth and survival, nutrient metabolism, immunosuppression, aging, as well as cancers (Guertin and Sabatini, 2007). Moreover, the mTOR pathway is activated by TNFα to promote angiogenesis (Lee et al., 2007a), which facilitates the chronic inflammation-induced cancers, including breast cancers (Lee et al., 2007a) and esophageal cancers (EC) (Hildebrandt et al., 2009; Yen et al., 2008).

The Hedgehog (HH) signal pathway is also considered to be crucially involved in the development of esophageal cancers because it is over-activated and correlated with lymph node metastasis as well as tumor development in esophageal cancers (Katoh and Katoh, 2009a; Lee et al., 2009). The HH pathway was identified first in *Drosophila* as an important regulator for proper embryonic patterning and is highly conserved from *Drosophila* to mammals (Ingham and McMahon, 2001). Three HH ligands have been identified in mammals: Sonic Hedgehog (SHH), Indian Hedgehog (IHH), and Desert Hedgehog (DHH) (Ng and Curran, 2011), which are secreted and initiate signaling in receiving cells by binding and inactivating the HH receptor Patched 1 (PTCH1) Inhibition of PTCH1 releases the G-coupled receptor-like signal transducer Smoothened (SMO). SMO then activates glioma-associated oncogenes (Gli) through blocking their inhibitory partner, suppressor of fused (SuFu) (Ng and Curran, 2011). Gli proteins, including Gli1, 2, and 3, are zinc finger transcription factors. Activated Gli proteins translocate into nucleus and stimulate the transcription of HH pathway target genes, including Gli1, PTCH1, and many survival-promoting molecules (Jiang and Hui, 2008; Ng and Curran, 2011). Besides being activated by the HH ligand-PTCH1-SMO axis, also known as the canonical HH pathway (Jenkins, 2009), Gli proteins, mainly Gli1, have been reported to be activated by AKT (Katoh and Katoh, 2009b; Stecca et al., 2007), MAPK/ERK (Seto et al., 2009), and KRAS (Nolan-Stevaux et al., 2009) in an HH ligand-PTCH1-SMO axis-independent or SMO-independent manner (Ng and Curran, 2011). Although the canonical pathway has been well established, how Gli1 is regulated in a SMO-independent manner is still a puzzle.

Although both mTOR and HH pathways have been considered as drug targets in gastrointestinal cancer, including esophageal cancers (Wiedmann and Caca, 2005), the correlation between the two pathways has not yet been reported. Additionally, whether there is a relationship between TNFα and HH pathway in EAC is also not clear. Therefore, in certain aspects this invention determined a novel role of the TNFα/mTOR pathway in the activation of HH pathway in EAC.

Figures 8A, 8B:
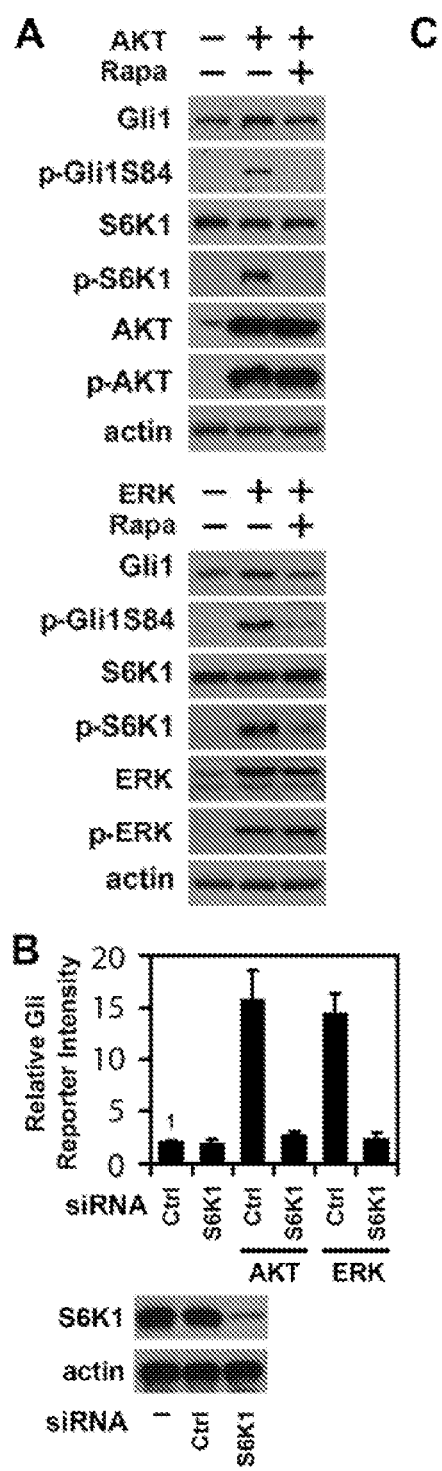
FIGS. 8A-8C. AKT and ERK can activate Gli1 through mTOR/S6K1 pathway.
Figure 8C:
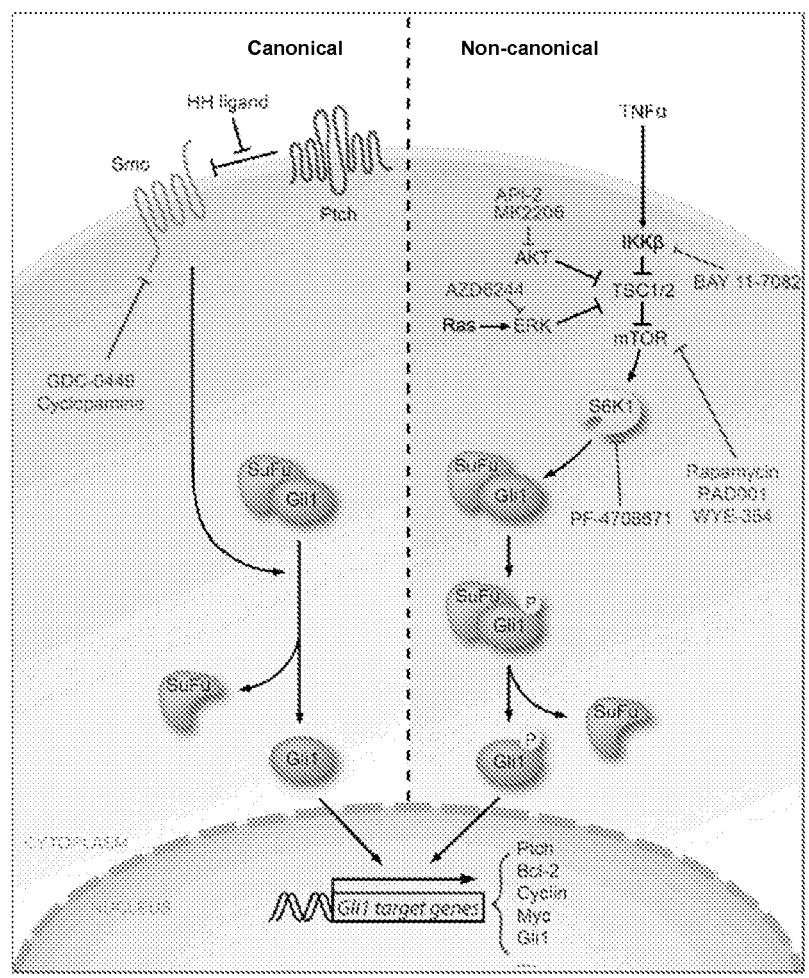

In examples of the instant invention, a SMO-independent activation of Gli1 by mTOR/S6K1 pathway was demonstrated, in which activated S6K1 phosphorylates Gli1 at Ser84 resulting in its release from SuFu binding and translocation into the nucleus to activate its target genes (FIG. 8C). The mTOR/S6K1 pathway was found to facilitate progression from inflammation and tumorigenesis through upregulation of VEGF as well as the subsequent angiogenesis (Lee et al., 2007a). In addition, TNFα/mTOR can be activated by chronic inflammation in the esophagus (Yen et al., 2008). The examples herein further imply that the mTOR/S6K1 pathway might also promote EAC through the activation of Gli1. Since Gli1 is known as an oncogene (Ng and Curran, 2011), these results also provide further evidence to support the concept that chronic inflammation is an important stimulator for tumorigenesis of the esophagus (Lambert and Hainaut, 2007a; Lambert and Hainaut, 2007b).

The canonical HH pathway is well known to have a tight negative feedback regulation, which blocks the HH ligands and inhibits SMO activation through Gli1-promoted transcription of PTCH and hedgehog interacting protein (Katoh and Katoh, 2006). When SMO is inactivated, SuFu binds to and inhibits Gli1 function (Katoh and Katoh, 2006). Loss-of-function mutation of SuFu has been shown to result in tumorigenesis due to the aberrant activation of the HH pathway (Cheng and Yue, 2008; Lee et al., 2007b). Therefore, SuFu is an important negative regulator for the HH pathway and acts as a tumor suppressor. In studies presented here, the inventors found that the phosphorylation of Gli1 by S6K1 blocked the interaction between SuFu and Gli1, allowing Gli1 to translocate into the nucleus to activate transcription of HH target genes. Thus, in contrast to the canonical HH pathway, SMO inhibitors seem not to affect S6K1-mediated Gli1 activation, suggesting that the S6K1-mediated release of SuFu from Gli1 occurs independently of SMO. In fact, SMO inhibitors, such as cyclopamine and GDC-0449, had little effects on the mTOR/S6K1-mediated Gli1 activation. These findings suggest that the mTOR/S6K1 pathway can act as a positive modulator to amplify and fuel Gli1 activation to promote tumorigenesis and disease progression.

Figures 7A, 7B, 7C, 7D, 7E, 7F, 7G:
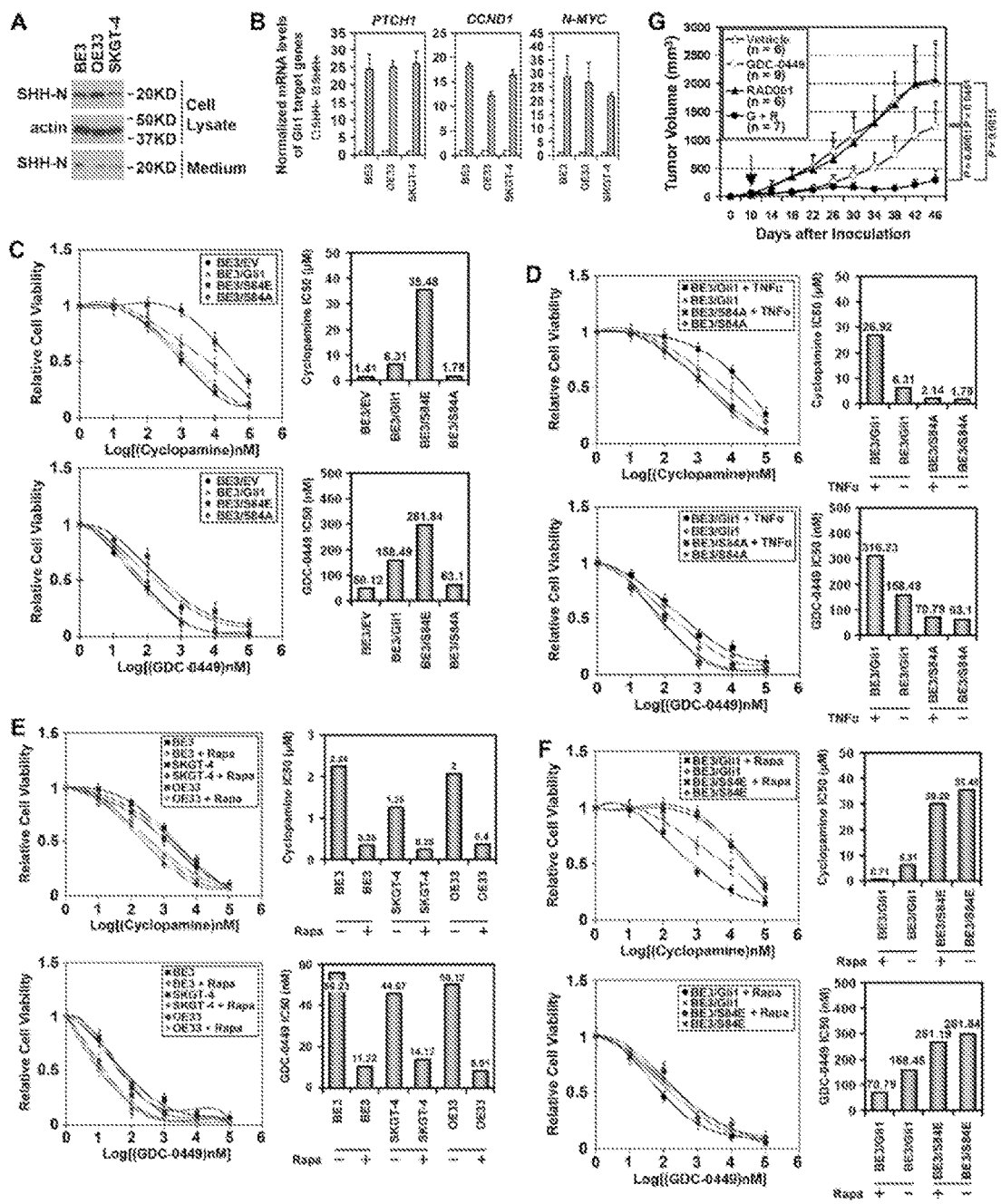
FIGS. 7A-7G. Effects of mTOR and/or HH pathway inhibitors on EAC cells.

The HH pathway has been considered as a therapeutic target for GI cancers, including esophageal cancers (Lee et al., 2009; Wiedmann and Caca, 2005). Several SMO inhibitors, including GDC-0449, are currently being tested in clinical trials, which are either structurally derived from or functionally similar to cyclopamine (Scales and de Sauvage, 2009; Stanton and Peng, 2010). These examples showed that the administration of GDC-0449 indeed decreased the EAC tumor size, indicating that GDC-0449 could also be used for treating EAC (FIG. 7G). In this study, however, the inventors disclose a SMO-independent activation of Gli1 by the mTOR/S6K1 pathway, which cannot be inhibited by SMO inhibitors, but is sensitive to inhibitors of mTOR pathways. Co-treatment with mTOR/S6K1 and SMO inhibitors, RAD001 and GDC-0449, indeed showed better inhibitory effects on tumor growth in vivo than single drug treatment. Therefore these results strongly suggest that a combination of inhibitors targeting the two pathways may be a more effective strategy to treat EAC.

In addition, through the immunostaining analysis of human EAC tissues, it was found that in about 40% (28/70) of patients, all of p-Gli1, Gli1, and p-S6K1 were positive. It appears that these patients might bear both canonical HH pathway and mTOR/S6K1-mediated SMO-independent Gli1 activation, which suggests that they might not be eligible for GDC-0449 treatment alone, but could benefit from the proposed co-treatment of inhibitors targeting both mTOR and HH pathways. Therefore, a pre-selection procedure might be used for the patients before receiving the SMO inhibitors to determine whether the co-treatment strategy should be applied. For example, determination of whether a patient's tumor is positive for phosphorylated-S6K and/or Gli1 activation (nuclear localization) or expression will be predictive for whether or not the patient will respond to inhibitors to the Hedgehog pathways, i.e., if the patient's tumor shows expression of both phosphorylated-S6K and Gli1 activation/expression, it is predicated that inhibition of the Hedgehog pathway alone would not be sufficient and combination therapy would be recommended. Thus, phosphorylated-S6K and/or Gli1 activation/expression can serve as a signature to determine the response to inhibitors to the HH pathway or the TNFα/mTOR/S6K1, or a combination therapy inhibiting both pathways.

Thus, in some aspects a method of the embodiments comprises treating cells in a subject by the use of at least two agents, in particular a signaling inhibitor of the Hedgehog pathway and a signaling inhibitor of the mTOR pathway if needed. Treatment with the first therapeutic agent may precede or follow the second therapeutic agent by intervals ranging from minutes to weeks. In certain embodiments, one would generally ensure that a significant period of time did not expire between the times of each delivery, such that the agents would still be able to exert an advantageously combined effect on the cell. For example, it is contemplated that one may administer two, three, four, or more doses of the first therapeutic agent substantially simultaneously (i.e., within less than about a minute) with the second therapeutic agent. In other aspects, the second therapeutic agent may be administered within about 1 minute to about 48 hours or more prior to and/or after administering the first therapeutic agent, or prior to and/or after any amount of time not set forth herein. In certain other embodiments, the first therapeutic agent may be administered within from about 1 day to about 21 days prior to and/or after administering another therapeutic modality. In some situations, it may be desirable to extend the time period for treatment significantly, however, where several weeks (e.g., about 1 to 8 weeks or more) lapse between the respective administrations. Various combinations may be employed, the first therapeutic agent is "A" and the secondary agent is "B":

A/B/A B/A/B B/B/A AJAJB A/B/B BIAJA A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the first or second therapeutic agent to a patient will follow general protocols for the administration of chemotherapeutics, taking into account the toxicity, if any, of these agents. It is expected that the treatment cycles would be repeated as necessary. It also is contemplated that various standard therapies, as well as surgical intervention, may be applied in combination with the first therapeutic, second therapeutic, or a combination thereof. These therapies include but are not limited to additional drug therapy, chemotherapy, additional radiotherapy, immunotherapy, gene therapy, and surgery.

It is worthwhile to mention that many inhibitors targeting these two pathways are being tested in clinical trials, such as GDC-0449 and IPI-926, targeting the hedgehog pathway (Stanton and Peng, 2010), and RAD001 and AP23573, targeting the mTOR pathway (Konings et al., 2009). Thus, a vast array of possible therapeutic combinations will be useful to simultaneously target these pathways.

Although SMO inhibitors are known to inhibit several types of cancer and have shown hopeful tumor-inhibitory effects, the development of resistance has been reported due to the constitutive activation mutation of SMO or overactivation of PI3K/AKT pathway (Metcalfe and de Sauvage, 2011). Buonamici et al. further showed that the resistance of medulloblastoma to SMO inhibitors could be decreased through a combination of SMO and PI3K/AKT inhibitors (Buonamici et al., 2010). Interestingly, PI3K/AKT and RAS/MEK/ERK have also been found to activate Gli1 in a SMO-independent manner (Katoh and Katoh, 2009b; Seto et al., 2009; Stecca et al., 2007) though the mechanisms are not well understood. Because AKT and ERK can activate the mTOR/S6K1 pathway (Ma et al., 2005; Ozes et al., 2001) and activation of Gli1 by AKT or ERK requires S6K1 (FIG. 8B), the finding that S6K1 phosphorylates Gli1 and enhances its function provides a molecular mechanism not only for mTOR/S6K1-mediated but also AKT or ERK-induced SMO-independent Gli1 activation (FIG. 8C). Thus, the results in the Examples also provide a potential explanation for the resistance of tumor cells to SMO inhibitors. Similarly, the study in the Examples offers a rationale for combining SMO with mTOR/S6K1 inhibitors to increase the effectiveness for treating subjects that have diseases or cancers, such as EAC, wherein the disease or cancer has Gli1 as a target regulated by both SMO-mediated signaling and mTOR-mediated signaling.

Thus, aspects of the invention provide Gli1 as a substrate for S6K1 and establish a crosstalk between the mTOR/S6K1 and HH pathways, suggesting a mechanism for SMO-independent Gli1 activation. The data also suggest that the combination of the inhibitors to these two pathways has a more potent inhibitory effect on the EAC cells than single agent alone. Moreover, the correlation between p-S6K1 and Gli1 of multiple cancer types using tissue microarray was also found, indicating that the combined targeted therapy, targeting both the mTOR/S6K1 and HH pathways, may be effective for treatment of EAC as well as other cancers.

In certain aspects, the mTOR inhibitors may include S6K1 inhibitors, AKT inhibitors, ERK inhibitors or IKKβ inhibitors. Examples of S6K1 inhibitors include PF-4708671 (Pearce et al.). Examples of AKT (also known as protein kinase B) inhibitors include, but are not limited to, e.g., Akt-1-1 (inhibits Akt1) (Barnett et al., 2005); Akt-1-1,2 (inhibits Ak1 and 2) (Barnett et al., 2005); API-59CJ-Ome (e.g., Jin et al., 2004); I-H-imidazo[4,5-c]pyridinyl compounds (e.g., WO05011700); indole-3-carbinol and derivatives thereof (e.g., U.S. Pat. No. 6,656,963; Sarkar and Li, 2004); perifosine (e.g., interferes with Akt membrane localization; Dasmahapatra et al., 2004); phosphatidylinositol ether lipid analogues (e.g., Gills and Dennis, 2004); triciribine (TCN or API-2 or NCI identifier: NSC 154020; Yang et al., 2004); or MK2206.

Exemplary ERK inhibitors include PD98059 (see, e.g., Zhu et al., 2004), U0126 (see, e.g., Zhu, et al., 2004), FR180204 (see, e.g., Ohori, 2008), sunitinib (see, e.g., US 2008/004287 incorporated herein by reference), sorafenib (see, e.g., US 2008/004287), Vandetanib (see, e.g., US 2008/004287), pazopanib (see, e.g., US 2008/004287), Axitinib (see, e.g., US 2008/004287) and PTK787 (see, e.g., US 2008/004287), or AZD6244. Exemplary IKKβ inhibitors include BAY 11-7082, parthenolide, or IMD 0354.

Compounds, such as the various mTOR inhibitors or SMO inhibitors of the present embodiments may also exist in prodrug form. Since prodrugs are known to enhance numerous desirable qualities of pharmaceuticals (e.g., solubility, bioavailability, manufacturing, etc.), the compounds employed in some methods of the embodiments may, if desired, be delivered in prodrug form. In general, such prodrugs will be functional derivatives of the metabolic pathway inhibitors of the embodiments, which are readily convertible in vivo into the active inhibitor. Conventional procedures for the selection and preparation of suitable prodrug derivatives are described, for example, in "Design of Prodrugs", ed. H. Bundgaard, Elsevier, 1985; Huttunen et al., 2011; and Hsieh et al., 2009, each of which is incorporated herein by reference in its entirety.

A prodrug may be a pharmacologically inactive derivative of a biologically active inhibitor (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality. Thus, prodrugs of the compounds employed in the embodiments may be prepared by modifying functional groups present in the compound in such a way that the modifications are cleaved, either in routine manipulation or in vivo, to the parent compound. Prodrugs include, for example, compounds described herein in which a hydroxy, amino, or carboxy group is bonded to any group that, when the prodrug is administered to a subject, cleaves to form a hydroxy, amino, or carboxylic acid, respectively. Thus, the invention contemplates prodrugs of compounds of the present embodiments as well as methods of delivering prodrugs.

The subject to be treated may be any animal, such as a human, a mouse, a rat, or any other mammal. The subject may have a tumor such as an esophageal tumor (particularly EAC), neuroendocrine tumor, breast tumor, lung tumor, prostate tumor, ovarian tumor, brain tumor, liver tumor, cervical tumor, colon tumor, renal tumor, skin tumor, head and neck tumor, bone tumor, bladder tumor, uterine tumor, lymphatic tumor, stomach tumor, pancreatic tumor, testicular tumor, leukemia, or lymphoma. The tumor may include benign tumor, pre-malignant tumor, cancer, or metastatic cancer. In addition, the tumor may specifically be of the following histological type, though it is not limited to these: neoplasm, carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. The subject may have gastrointestinal tract disease, such as a tumor or any disease of the esophagus, stomach, duodenum, and intestine, such as Barrett's esophagus.

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

TNFα Promotes Gli1 Activity Through the mTOR Pathway

Figures 1A, 1B, 1C, 1D, 1E:
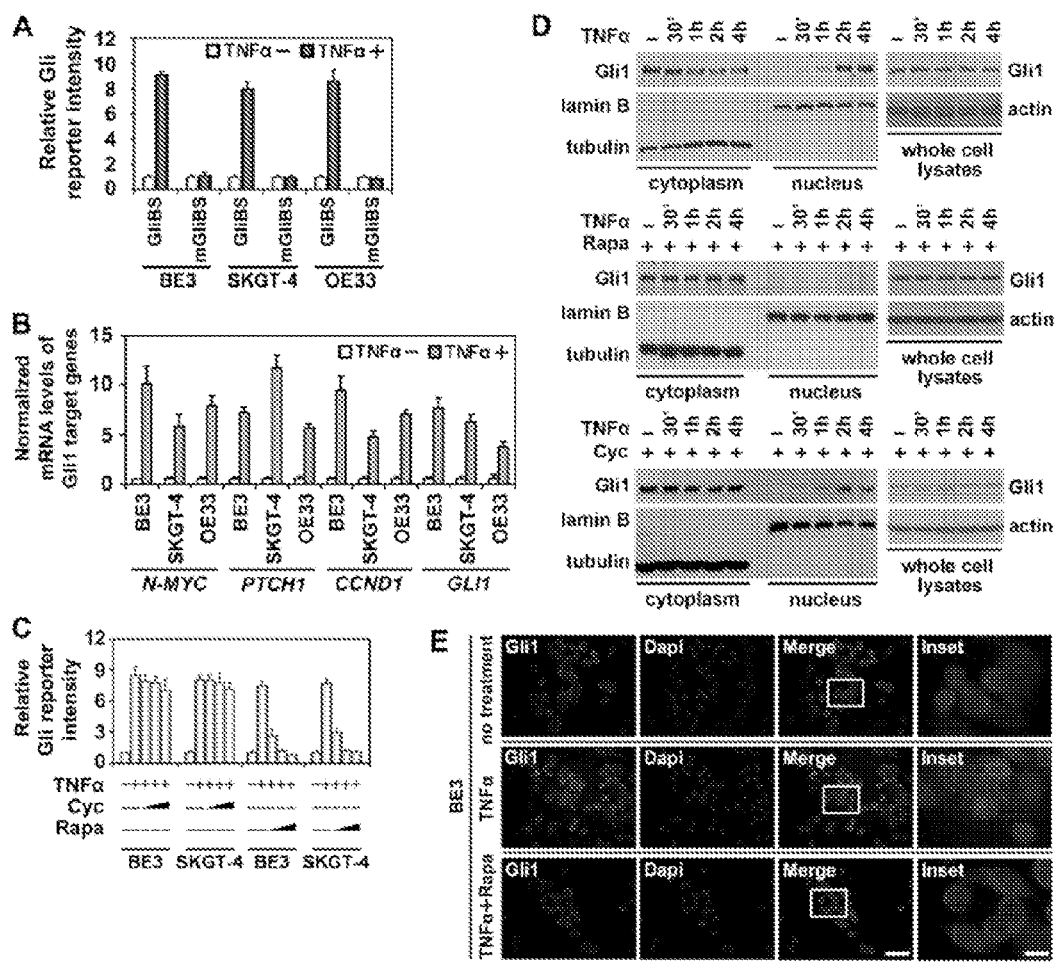
FIGS. 1A-1E. TNFα regulates Gli1 transcriptional activity.
Figures 9A, 9B, 9C, 9D, 9E, 9F, 9G, 9H:
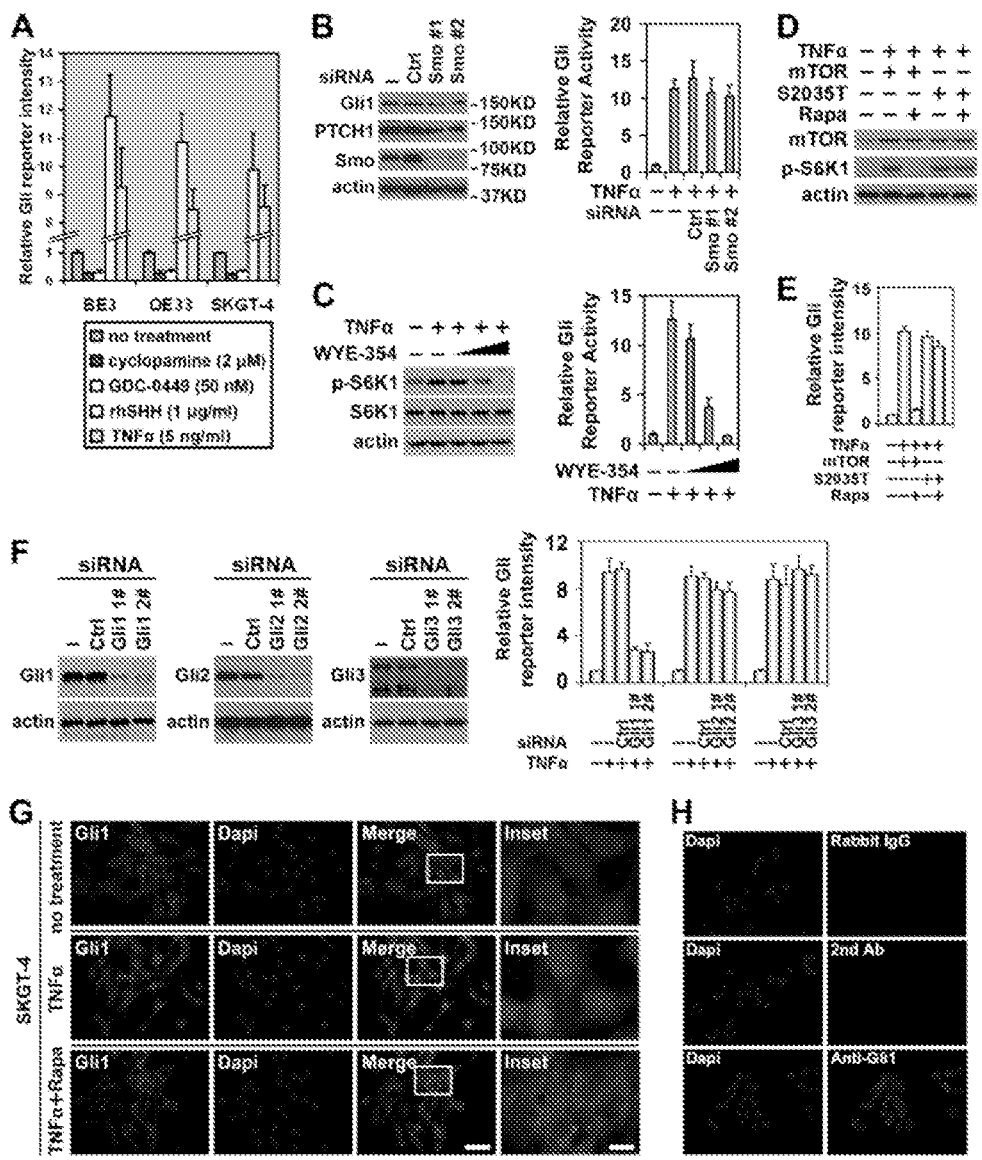
FIGS. 9A-9H. related to FIG. 1. TNFα regulates Gli1 transcriptional activity.

Because Gli protein activity is a useful readout for the HH pathway (Jiang and Hui, 2008), the inventors employed a Gli-dependent luciferase reporter system (Sasaki et al., 1997) to evaluate the influence of TNFα on the HH pathway in three EAC cell lines, BE3, SKGT-4, and OE33 (Boonstra et al., 2010). The inventors observed that TNFα increases the intensity of the reporter (FIG. 1A) and the mRNA levels of four Gli target genes (FIG. 1B). Therefore, TNFα can activate the HH pathway in the EAC cells. Then, the inventors compared the activity of HH pathway in EAC cells stimulated by SHH or TNFα. The inventors found that there is constitutive activation of HH pathway in EAC cell lines, which can be inhibited by SMO inhibitors, cyclopamine and GDC-0449 (Scales and de Sauvage, 2009). Both SHH and TNFα increased the activity of HH pathway in EAC cells with higher intensity from SHH (FIG. 9A).

To investigate whether TNFα-induced Gli activity is through SMO-dependent HH pathway, the inventors pretreated the EAC cells with cyclopamine followed by TNFα. Interestingly, cyclopamine did not affect the TNFα-induced Gli activity (FIG. 1C). Similarly, knock-down of SMO did not inhibit the TNFα-induced Gli activity either (FIG. 9B). Therefore, TNFα activates Gli function in a SMO-independent manner. To determine whether the mTOR pathway is involved in the regulation of Gli function by TNFα, the inventors used rapamycin to block the mTOR pathway (Wullschleger et al., 2006). Surprisingly, rapamycin impaired TNFα-stimulated Gli activation (FIG. 1C). Similar results were observed with WYE-354, an mTOR ATP competitive inhibitor (FIG. 9C). Therefore, TNFα-stimulated Gli activation might require the activation of the mTOR pathway. To further evaluate this possibility, the inventors overexpressed wild-type mTOR or a rapamycin-resistant mTOR (mTORS2035T) (Brown et al., 1995) in EAC cells followed by treatment of TNFα alone or plus rapamycin. Western blot results confirmed that rapamycin blocked activation of the mTOR pathway in mTOR-overexpressed cells but not in mTORS2035T-overexpressed cells (FIG. 9D). Consistently, rapamycin suppressed the TNFα-stimulated Gli reporter expression in mTOR-transfected EAC cells but barely had an effect on mTORS2035T-transfected EAC cells (FIG. 9E). Collectively, these results suggest that TNFα activates Gli proteins through the mTOR pathway.

Although Gli1, Gli2, and Gli3 all can regulate the Gli reporter (Jiang and Hui, 2008; Ng and Curran, 2011), only Gli1 knock-down was found to impair the TNFα-stimulated Gli activation (FIG. 9F), which suggests that TNFα selectively activated Gli1. Likewise, TNFα treatment rapidly induced Gli1 nuclear accumulation without obvious changes in the total protein level of Gli1 (FIG. 1D, top panel). Rapamycin (FIG. 1D, middle panel), but not cyclopamine (FIG. 1D, bottom panel), blocked TNFα-induced Gli1 nuclear accumulation, which was further supported by the immunofluorescence staining (FIG. 1E and FIGS. 9G and 9H). Therefore, TNFα promotes Gli1 nuclear localization and activation through the mTOR pathway.

Example 2

S6K1 Mediates the Regulation of Gli1 by TNFα

Figures 2A, 2B, 2C, 2D, 2E, 2F, 2G:
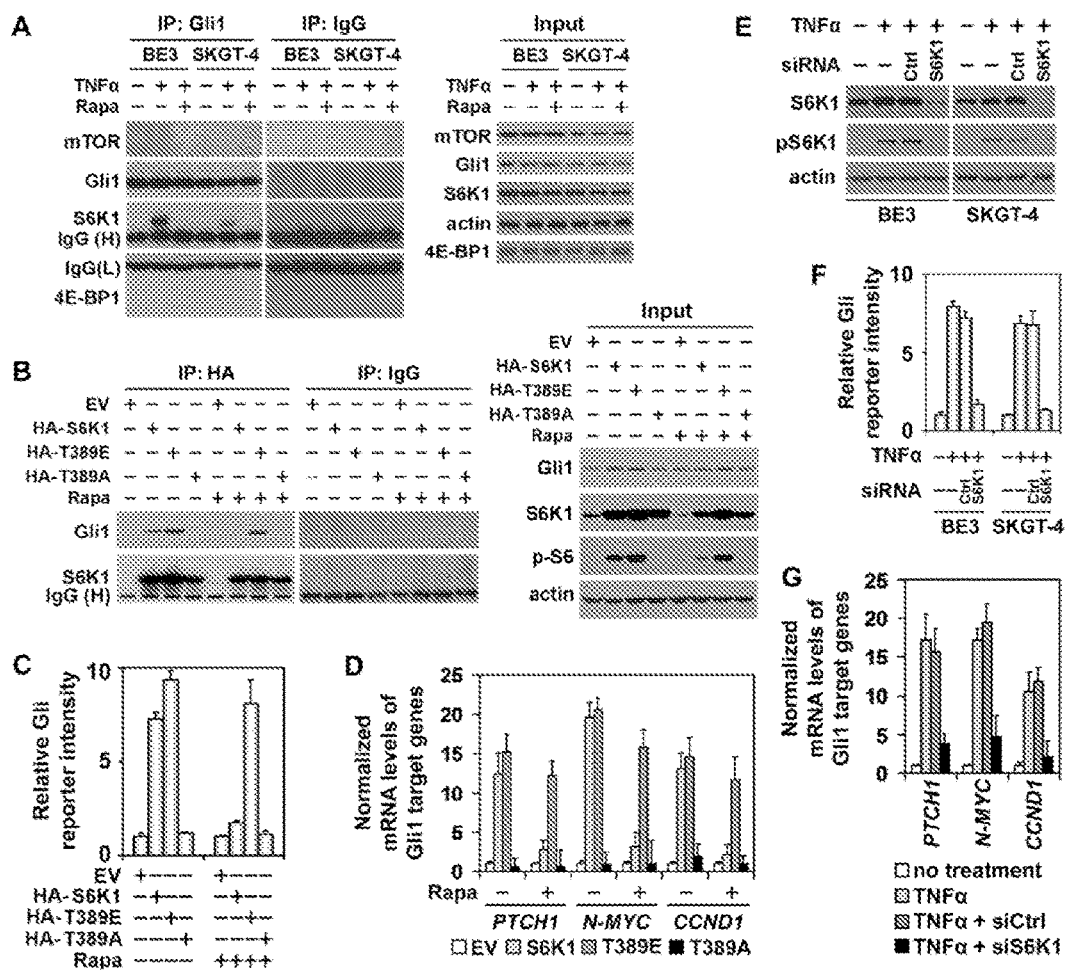
FIGS. 2A-2G. S6K1 mediates the regulation of Gli1 by TNFα.
Figures 10A, 10B, 10C, 10D, 10E, 10F:
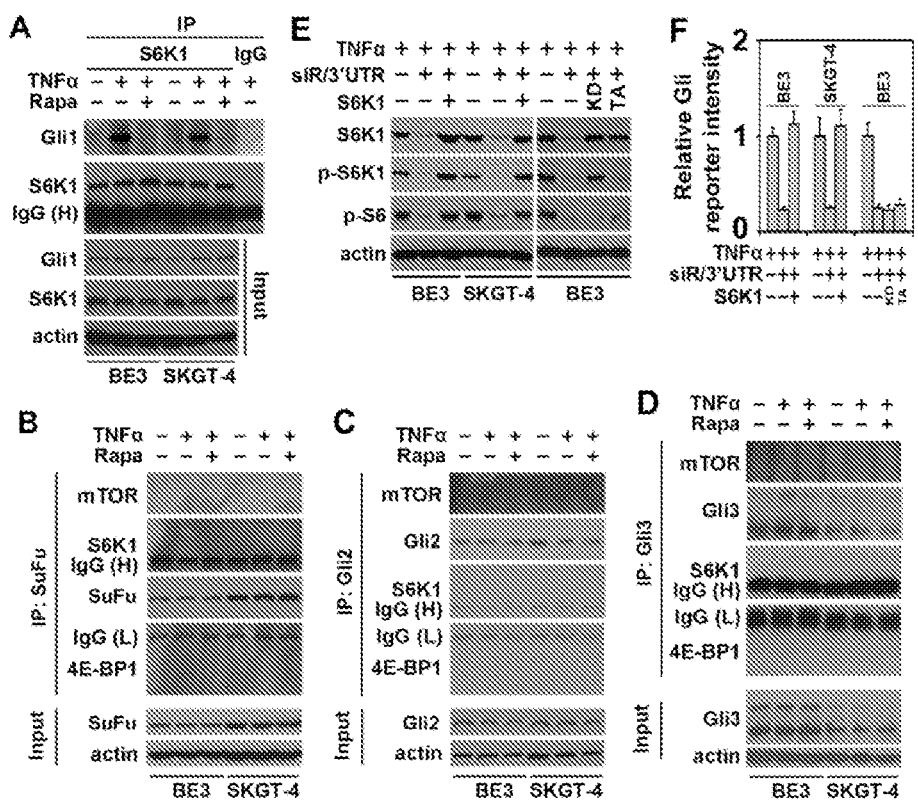
FIGS. 10A-10F. related to FIG. 2. S6K1 mediates the regulation of Gli1 by TNFα.

To investigate how the mTOR pathway activates Gli1 activity, it was examined whether Gli1 interacts with the components of mTOR pathway. Without TNFα, no interactions were found between Gli1 and mTOR pathway components; with TNFα stimulation, however, a clear interaction was observed between Gli1 and S6K1, but not between Gli1 and mTOR or 4EB-P1 (FIG. 2A and FIG. 10A). Since Gli1 function is inhibited by SuFu, it was also examined whether there are any interactions between mTOR pathway components and SuFu. Unlike Gli1, SuFu did not interact with mTOR, S6K1, or 4EB-P1, regardless of TNFα treatment or not (FIG. 10B). Moreover, neither Gli2 nor Gli3 bound to mTOR, S6K1, or 4EB-P1 (FIGS. 10C and 10D). Taken together, the mTOR pathway might regulate Gli1 via S6K1.

Because S6K1 bound to Gli1 only under TNFα stimulation, it was hypothesized that S6K1 might need to be activated to interact with Gli1. To address this point, wild-type S6K1, constitutively activated S6K1 (S6K1T389E), or loss-of-function S6K1 (S6K1T389A) (Holz et al., 2005) was transfected into the BE3 cells. S6K1 and S6K1T389E increased S6K1 activity, as indicated by increase of phosphorylation of S6, a substrate of S6K1 (FIG. 2B). Rapamycin could inhibit the activity of S6K1, but not S6K1T389E (FIG. 2B) (Holz et al., 2005). Both S6K1 and S6K1T389E interacted with Gli1 and rapamycin effectively inhibited the interaction between S6K1 and Gli1, but not between S6K1T389E and Gli1 (FIG. 2B). In addition, ectopic expression of S6K1T389A did not interact with Gli1 (FIG. 2B). Furthermore, ectopic expression of S6K1 or S6K1T389E, but not S6K1T389A, increased the expression of Gli reporter and Gli1 target genes (FIGS. 2C and 2D). Rapamycin blocked the effects of S6K1 on Gli reporter expression, but did not affect that of S6K1T389E (FIGS. 2C and 2D). Thus, only the activated S6K1 formed a complex with Gli1 and enhanced its activity.

To investigate whether S6K1 mediates the regulation of Gli1 by TNFα, S6K1 was knocked down (FIG. 2E) and the regulation of Gli1 by TNFα was tested. The results indicated that the TNFα-stimulated Gli1 activity and expression of Gli target genes were impeded by S6K1 knock-down (FIGS. 2F and 2G). Additionally, the inhibition of TNFα-stimulated Gli1 activation by siRNA that targeted 3' UTR region of S6K1 mRNA was rescued by expression of an exogenous S6K1 lacking of 3' UTRs, but not by expression of exogenous S6K1T389A or a kinase-dead S6K1 (S6K1 K100R) (Holz et al., 2005) (FIGS. 10E and 10F). Therefore, activated S6K1 is required for the regulation of Gli1 by the TNFα/mTOR pathway.

Example 3

Figures 3A, 3B, 3C, 3D, 3E, 3F, 3G, 3H:
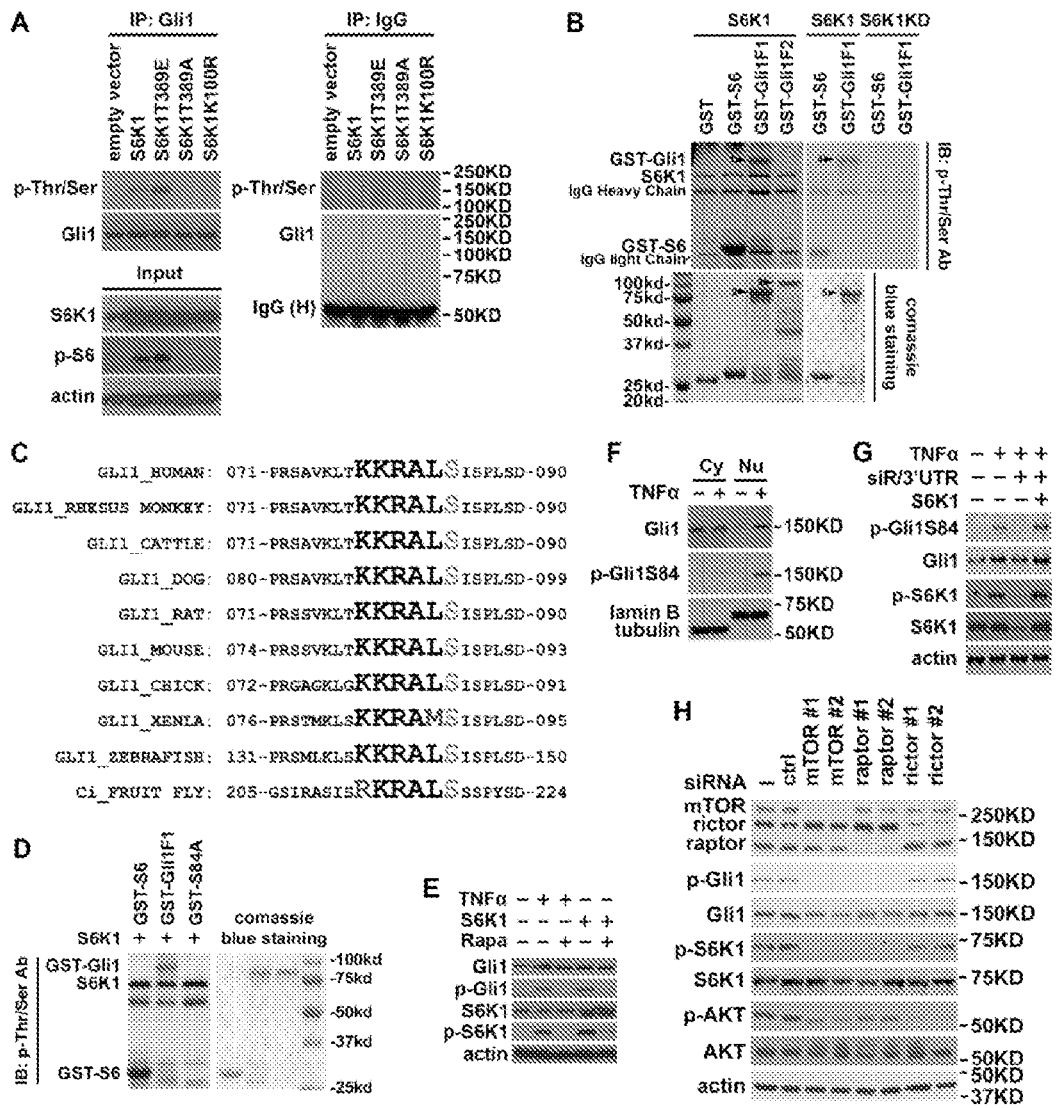
FIGS. 3A-3H. S6K1 phosphorylates Gli1 at Ser84.

Gli1 is Phosphorylated by S6K1 and Required for TNFα/mTOR/S6K1-Mediated Cell Proliferation Since S6K1 is a serine/threonine kinase, it was studies whether S6K1 regulates Gli1 through phosphorylation. Indeed, serine/threonine phosphorylation of Gli1 was observed with the ectopic expression of S6K1 or S6K1T389E (FIG. 3A), but neither S6K1T389A nor S6K1K100R (FIG. 3A). Furthermore, an in vitro kinase assay showed that only one of the Gli1 fragments containing amino acids 1-500, Gli1F1, was phosphorylated by S6K1 but not by S6K1K100R (FIG. 3B). The phosphorylation level of the Gli1F1 fragment was comparable to that of S6, suggesting that Gli1 was a substrate of S6K1 in vitro. 79-KKRALS-84 (SEQ ID NO: 1) was identified (FIG. 11A), which is highly conserved from fruit fly to human (FIG. 3C), as one potential S6K1-recognizing motif (K/RxRxxS/T; SEQ ID NO:2) in Gli1F1. When Ser84 was mutated to alanine (Gli1S84A), phosphorylation of Gli1 by S6K1 disappeared (FIG. 3D), suggesting that the Ser84 in Gli1 is the site phosphorylated by S6K1 in vitro.

Figures 11A, 11B, 11C, 11D, 11E, 11F, 11G, 11H, 11I:
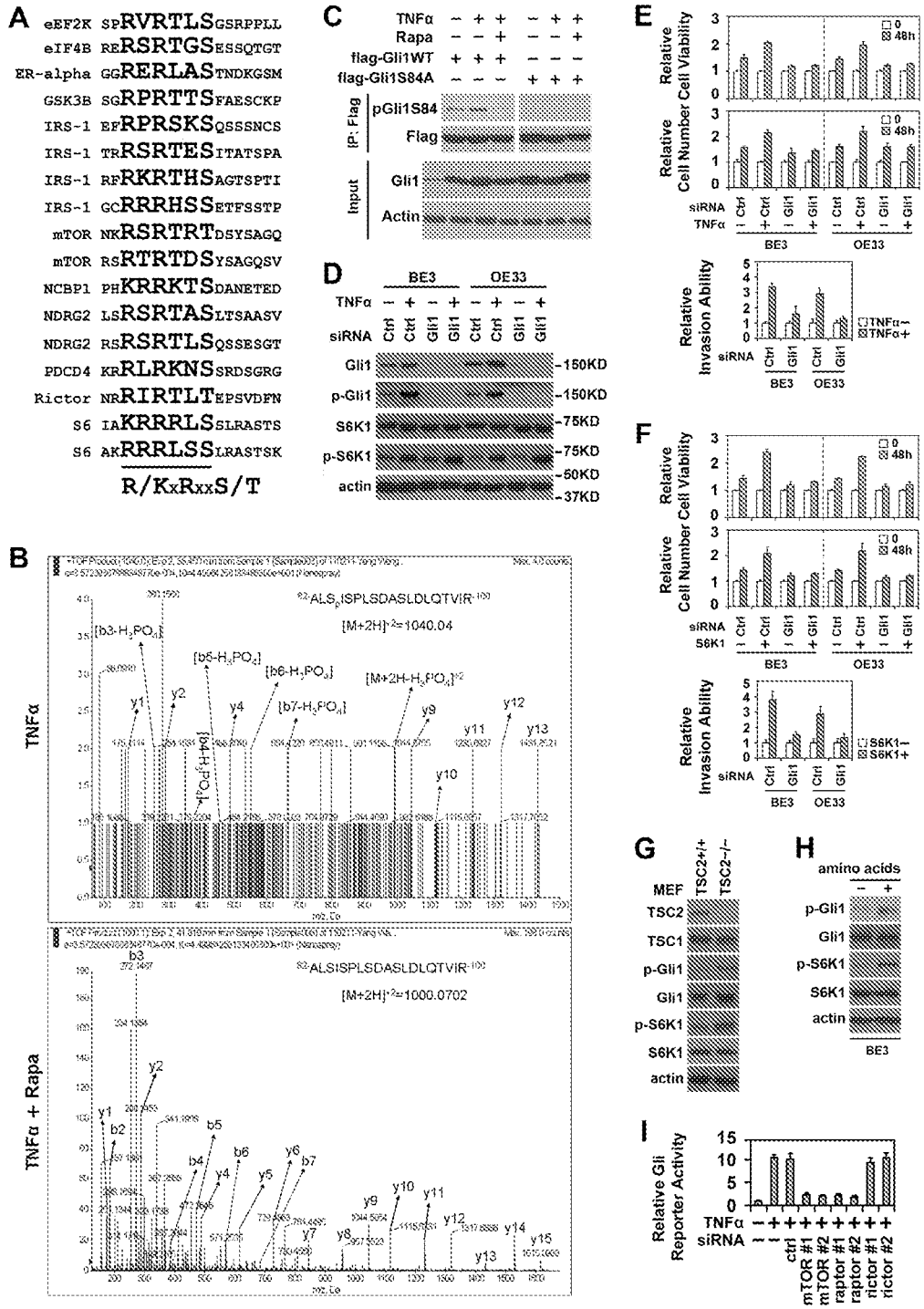
FIGS. 11A-11I. related to FIG. 3. S6K1 phosphorylates Gli1 at Ser84.

To assess whether this phosphorylation occurs in vivo, mass spectrometric analysis using BE3 cells treated with TNFα alone or TNFα and rapamycin was performed. The results showed that the phosphorylation of Gli1 Ser84 was detected in cells treated with TNFα but not in cells treated with rapamycin and TNFα (FIG. 11B). Thus, the activation of mTOR/S6K1 pathway contributes to the phosphorylation of Gli1 Ser84. To further investigate endogenous Gli1 phosphorylation by TNFα or S6K1, a mouse polyclonal antibody that specifically recognizes phosphorylated Ser84 of Gli1 (p-Gli1S84) was developed. This antibody recognized TNFα stimulated flag-Gli1, but not without TNFα or flag-Gli1S84A regardless of TNFα treatment (FIG. 11C). Using this antibody, TNFα stimulation or S6K1 ectopic expression effectively induced Gli1 Ser84 phosphorylation (FIG. 3E) was found, which was diminished by the addition of rapamycin (FIG. 3E). Notably, phosphorylated Gli1 was observed mainly in the nucleus (FIG. 3F), which implied that the phosphorylated Gli1 might be functionally activated. The TNFα-stimulated phosphorylation of Gli1 was largely inhibited when S6K1 was knocked down by siRNA targeting the 3' UTR, but could be effectively rescued by exogenous S6K1 (FIG. 3G). Together, the results suggest that S6K1 mediates the regulation of Gli1 by the TNFα/mTOR pathway through phosphorylating Gli1 at Ser84.

Then, it was studied if Gli1 activation is required for the effects of TNFα/mTOR/S6K1 pathway on cellular oncogenicity. Clear signals of p-Gli1S84 were detected in BE3 and OE33 (FIG. 11D) and knock-down of Gli1 impaired the TNFα-stimulated as well as S6K1 ectopic expression-increased cell viability, proliferation, and invasion (FIGS. 11E and 11F). Thus, the activation of Gli1 by S6K1 is functionally involved in the TNFα/mTOR pathway.

Besides TNFα, it was tested whether other mTOR pathway stimulators led to Gli1 phosphorylation. In $TSC2^{-/-}$ MEFs, which have constitutive activation of the mTOR pathway and S6K1, the phosphorylation of Gli1S84 increased compared with $TSC^{+/+}$ MEFs (FIG. 11G). Therefore, the regulation of Gli1 by S6K1 might also have a role in non-cancerous cells. It would be of interest to further investigate this possibility. Stimulation by amino acids also induced the phosphorylation of Gli1S84 (FIG. 11H). Therefore, the activation of the mTOR pathway is an important stimulator for Gli1 phosphorylation.

The mTOR pathway includes two complexes: mTOR complex 1 (mTORC1), which requires raptor and activates S6K1, and mTORC2, which requires rictor and activates AKT (Zoncu et al., 2011). Rapamycin and WYE-354 inhibit both mTORC1 and mTORC2 (Richard et al., 2010). Therefore, it was studied whether mTORC2 also regulates Gli1 phosphorylation. Although knock-down of mTOR or raptor impaired the TNFα-mediated Gli1 phosphorylation and activation, knock-down of rictor did not (FIGS. 3H and 11I), indicating that only mTORC1 plays a role in the regulation of Gli1.

Example 4

Figures 4A, 4B, 4C, 4D:
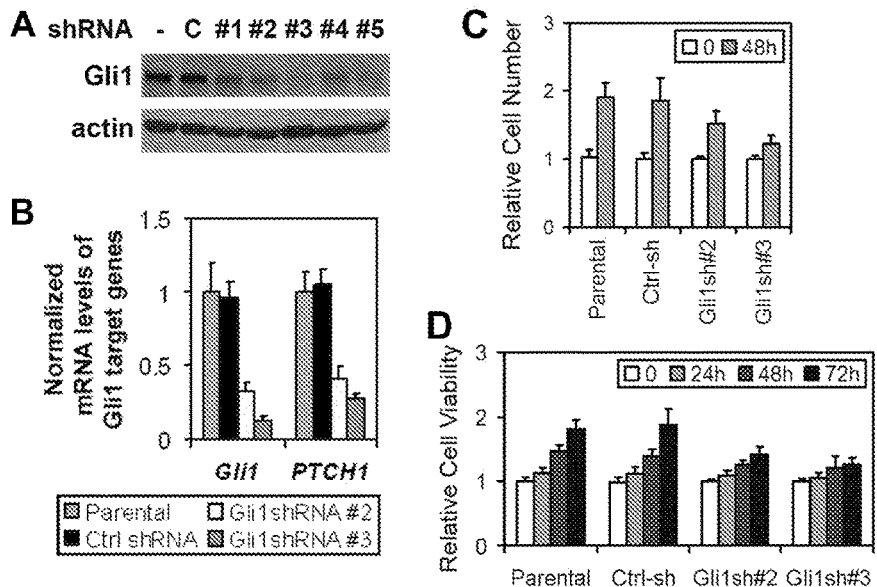
FIGS. 4A-4D. Knock-down of Gli1 in EAC cells decreases cell proliferation, migration, invasion, and colony formation.
Figures 5A, 5B, 5C, 5D, 5E, 5F:
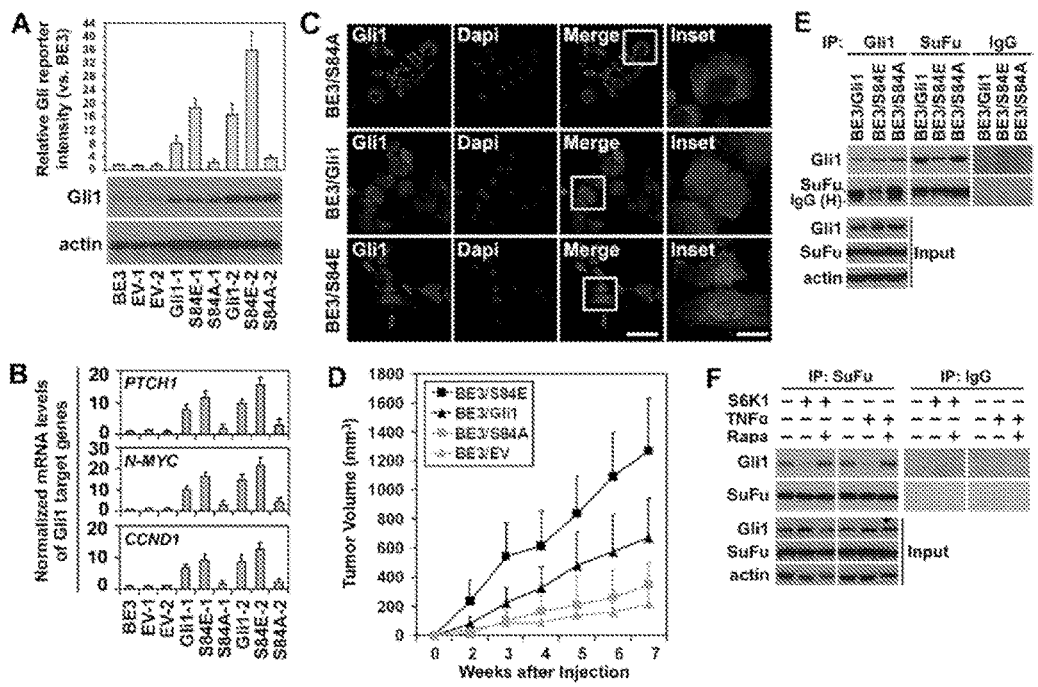
FIGS. 5A-5F. Functional effects of S6K1-mediated Gli1 phosphorylation.
Figures 12A, 12B, 12C:
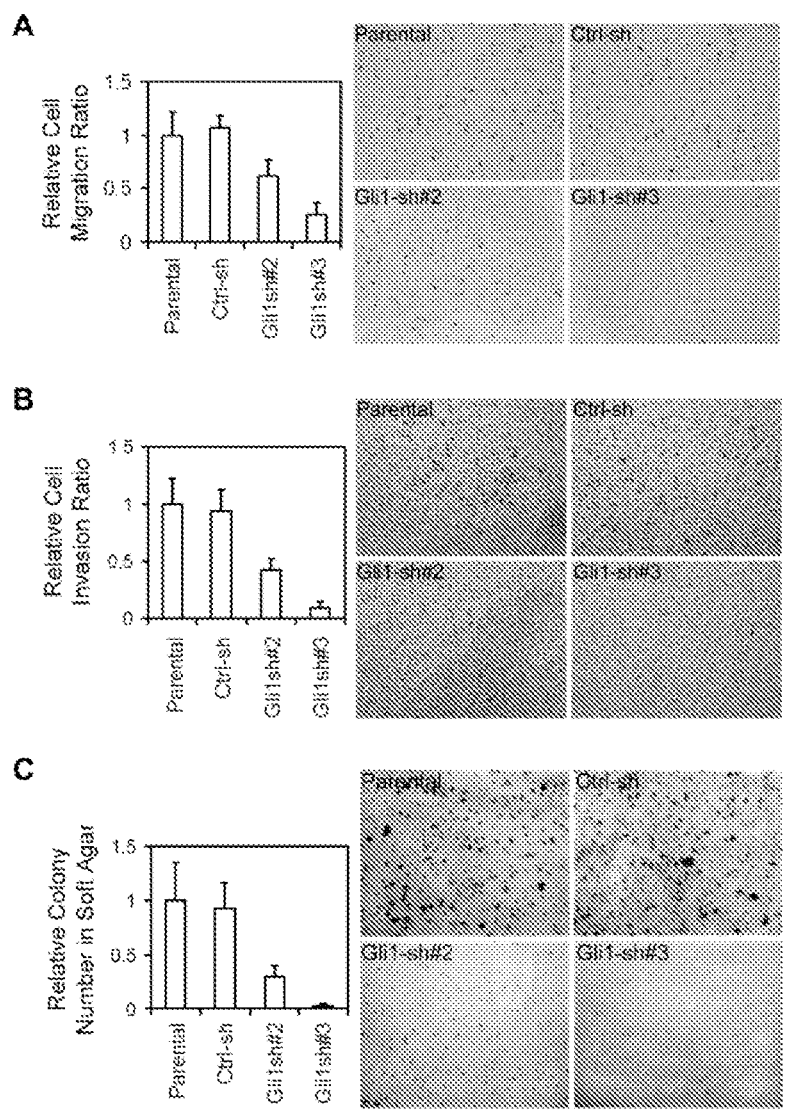
FIGS. 12A-12C. related to FIG. 4. Knock-down of Gli1 in EAC cells decreases migration, invasion, and colony formation. The EAC parent and stable cells with control siRNA and siRNA targeting Gli1 were counted and seeded on transwells for migration assays (FIG. 12A) or matrigel-covered transwells for invasion assays (FIG. 12B) or mixed with 0.5% agarose for soft agar assay (FIG. 12C). Error bars represent SD (n=3).
Figures 13A, 13B, 13C, 13D, 13E, 13F, 13G, 13H, 13I, 13J, 13K:
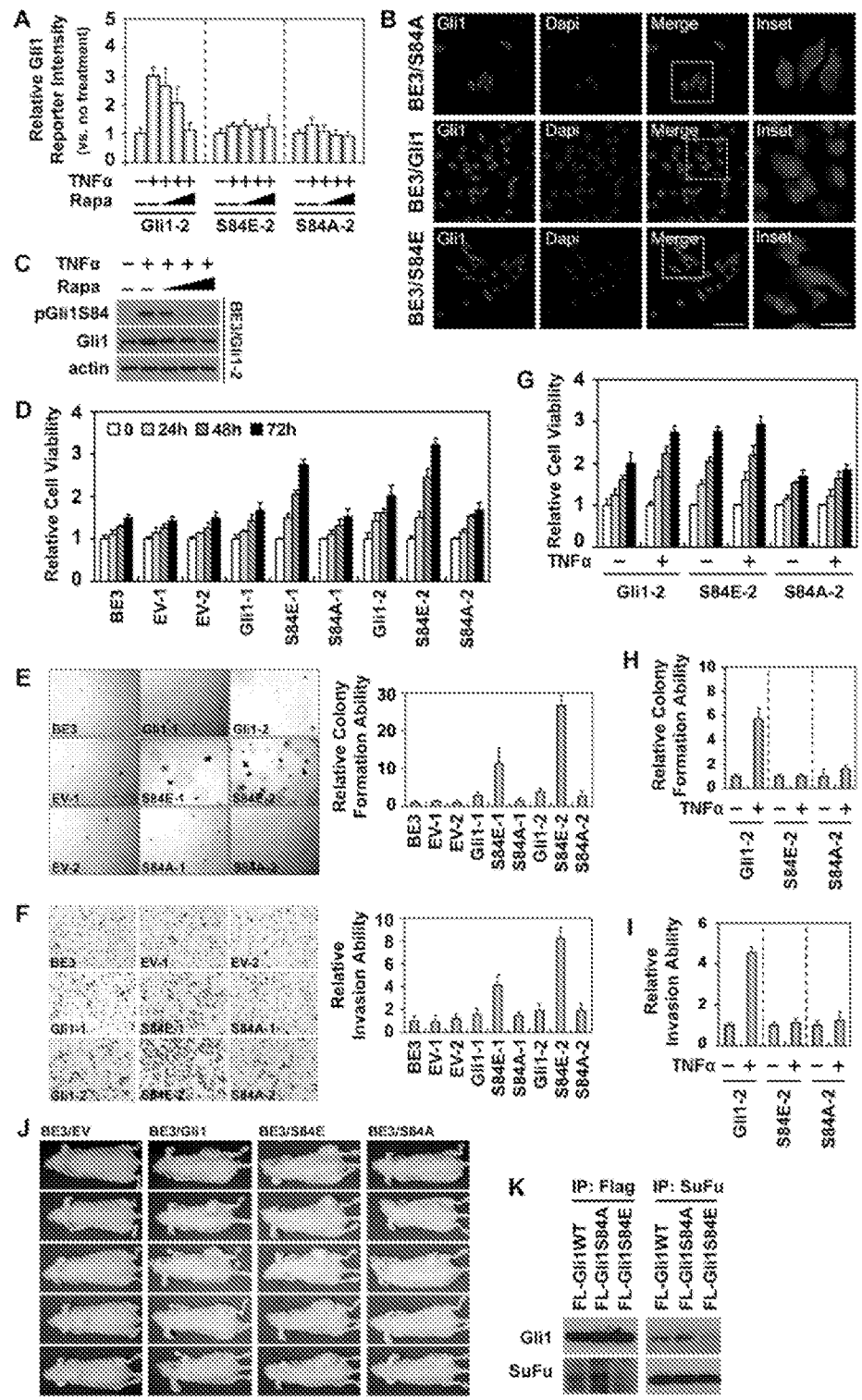
FIGS. 13A-13K. related to FIG. 5. Functional effects of S6K1-mediated Gli1 phosphorylation.

Gli1 Phosphorylation by S6K1 Augments the Gli1 Function and Inhibits SuFu Binding Since Gli1 is regulated by S6K1 in EAC cells, it was studied if Gli1 is required for EAC transformation. BE3 stable clones with Gli1 knock-down were established (FIG. 4A), and as expected, transcription of Gli1 target genes decreased with Gli1 knock-down (FIG. 4B). Moreover, Gli1 knock-down also decreased cell proliferation (FIGS. 4C and 4D), migration (FIG. 12A), invasion (FIG. 12B), and anchorage-independent growth ability (FIG. 12C). Thus, Gli1 is functionally required for EAC cells. Then, to understand the effects of Ser84 phosphorylation on Gli1 function, stable clones of BE3 cells expressing wild-type Gli1 (BE3/Gli1), Gli1S84A (BE3/S84A), Gli1S84E (BE3/S84E), or with the empty vector (BE3/EV) were generated. For Gli1S84E, Ser84 was mutated into glutamine to mimic constitutive phosphorylation of Gli1 at Ser84. It was found that with similar Gli1 expression levels, BE3/S84E bore much higher Gli1 transcriptional activity and mRNA levels of Gli1 target genes among all the stable clones (FIGS. 5A and 5B). Consistently, the immunofluorescence staining showed that the level of nuclear Gli1 was much higher in BE3/S84E cells than BE3/Gli1 and BE3/S84A (FIG. 5C). To further confirm that the functional difference was due to the mutations of Gli1, these cells were treated with TNFα alone or together with rapamycin and found that TNFα markedly induced the Gli1 transcriptional activity in BE3/Gli1, which was inhibited by co-treatment of rapamycin, but did not affect the Gli1 activity in BE3/S84E and BE3/S84A (FIG. 13A). The results suggest that both S84E and S84A mutants were insensitive to TNFα stimulation. The immunofluorescence staining also showed that in BE3/Gli1 Gli1 nuclear localization was induced by TNFα, but in BE3/S84E or BE3/S84A, Gli1 distribution was not obviously changed by TNFα (FIG. 5C and FIG. 13B). Moreover, the p-Gli1 S84 level also increased with TNFα stimulation but gradually decreased with increased rapamycin dose (FIG. 13C). Taken together, TNFα-stimulated S84 phosphorylation increases Gli1 nuclear localization and transcriptional activity, and S84E and S84A mutants, mimicking phosphorylated and non-phosphorylated Gli1, respectively, are no longer sensitive to TNFα.

Many reports have described Gli1 as an oncogene (Jiang and Hui, 2008; Ng and Curran, 2011), and hence, the relationship between Gli1 phosphorylation and its tumorigenic functions was investigated. Gli1S84E and wild-type Gli1, but not Gli1S84A, increased cell proliferation (FIG. 13D). The Gli1S84E stable clones also exhibited the highest level of colony formation activity in soft-agar assay (FIG. 13E). BE3/S84E exhibited much higher invasive ability than BE3/Gli1 and BE3/S84A (FIG. 13F). These results support that the phosphorylation of Gli1 at Ser84 enhances Gli1 function. To further address why the wild-type Gli1 did not show strong biological activities in FIGS. 13E-13F, the inventors treated the BE3/Gli1 stable clone with TNFα. Interestingly, the inventors observed increased cell proliferation, anchorage-independent growth and invasion (FIGS. 13G-13I). Notably, TNFα did not affect the BE3/S84E and BE3/S84A stable cells (FIGS. 13G-13I). Therefore, the TNFα/mTOR pathway promotes Gli1 function mostly via the Gli1 Ser84 phosphorylation. Furthermore, the inventors tested the tumorigenicity of these cells by subcutaneously injecting them into the nude mice. Consistent with the in vitro data, BE3/S84E had the strongest tumorigenicity among all stable cells. While BE3/Gli1 also led to tumor growth in nude mice, the tumors were smaller than those from BE3/S84E. BE3/EV and BE3/S84A induced only small tumor formation (FIG. 5D and FIG. 13J). All these data indicated that Gli1 Ser84 is a key site for Gli1 activity and its phosphorylation by S6K1 enhances Gli1 function as an oncogene.

It has been reported that without HH ligand stimulation, Gli1 function is inhibited by SuFu (Cheng and Yue, 2008). The inventors therefore investigated whether Gli1 Ser84 phosphorylation affects its binding with SuFu. Co-immunoprecipitation experiments showed that the interaction between SuFu and Gli1 was markedly decreased in BE3/S84E compared with BE3/Gli1 and BE3/S84A at a similar total level of SuFu (FIG. 5E), which suggested that the Ser84 phosphorylation in Gli1 possibly reduced its binding to SuFu. Similarly, SuFu strongly interacted with exogenous Gli1WT and Gli1S84A but only weakly with Gli1S84E (FIG. 13K). Furthermore, both TNFα treatment and S6K1 ectopic expression decreased the binding between SuFu and Gli1, which was fully reversed by rapamycin administration (FIG. 5F). Taken together, TNFα/S6K1-induced phosphorylation of Gli1Ser84 attenuates SuFu-mediated Gli1 inhibition.

Example 5

S6K1 and Gli1 are Positively Correlated in Human Tumor Tissues

Figures 14A, 14B, 14C, 14D, 14E, 14F, 14G, 14H, 14I:
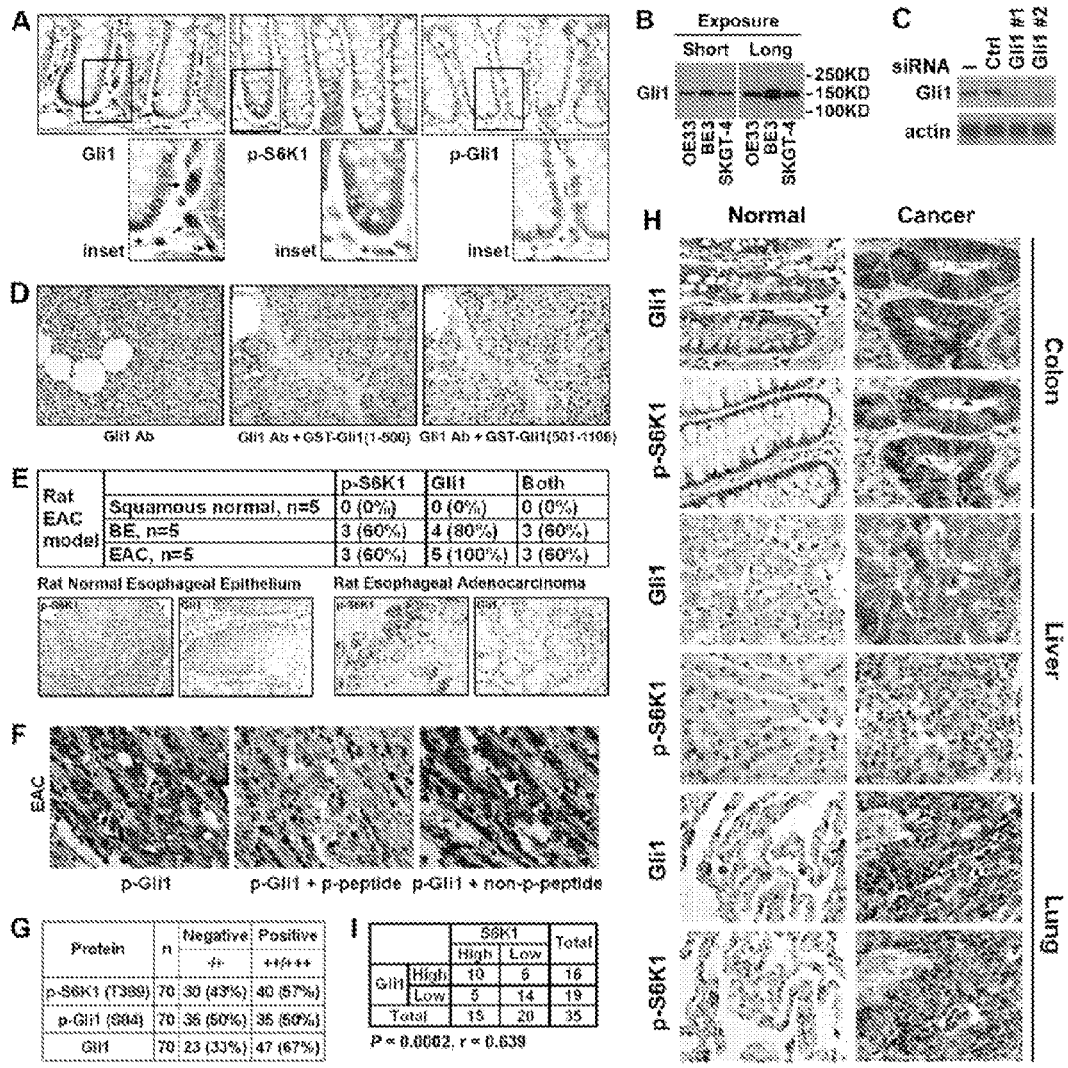
FIGS. 14A-14I. related to FIG. 6. Correlations between p-S6K1T389 and Gli1 or p-Gli1S84 in EAC.

Even though the anti-Gli1 antibody from Santa Cruz Biotechnology has been used for immunohistochemistry (IHC) before (Di Marcotullio et al., 2006; Fukaya et al., 2006), the inventors validated the specificity of the anti-Gli1 antibody again for IHC. The staining in normal mouse colon slides using this antibody showed that the Gli1 signal (brown color pointed by arrow) is mainly localized in stromal cells (FIG. 14A, left panel), which is consistent with the previous report (Kolterud et al., 2009). Furthermore, Western blot analysis in EAC cell lines showed a single band at about 150 kD (FIG. 14B), which is consistent with the Gli1 molecular weight. When Gli1 was knocked down, the signal detected by the antibody concomitantly decreased compared with that from the parental or control siRNA-transfected cells (FIG. 14C). This antibody was raised against amino acids 781-1080 of Gli1, and the inventors purified the GST-Gli1 protein to block the antibody affinity in IHC. The Gli1 staining was completely blocked GST-Gli1 fragment containing amino acids 501-1160, but not by the fragment containing amino acids 1-500 (FIG. 14D). Therefore, this anti-Gli1 antibody is applicable for IHC experiments.

Figures 6A, 6B, 6C, 6D, 6E, 6F, 6G:
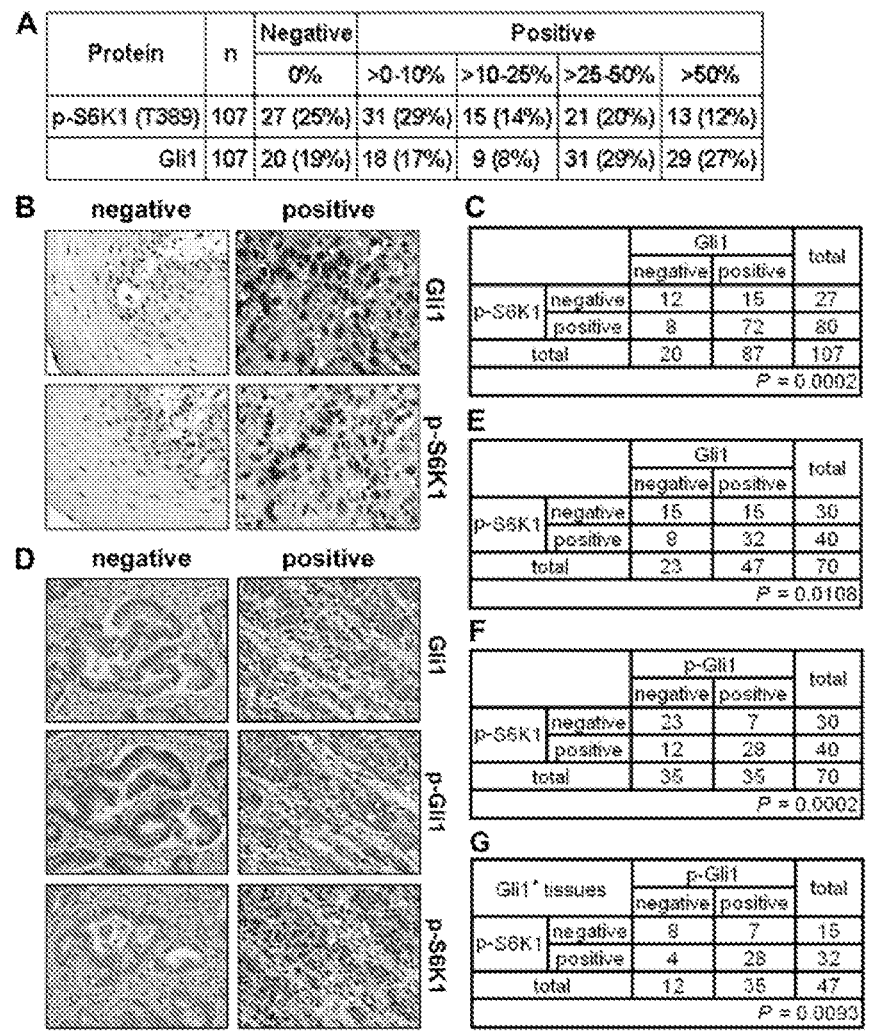
FIGS. 6A-6G. Correlations between p-S6K1T389 and Gli1 or p-Gli1S84 in EAC.

The inventors then evaluated the levels of Gli1 and p-S6K1 in 107 EAC tissue specimens by IHC (FIGS. 6A and 6B) to validate the significance of the regulation of Gli1 by S6K1 in human EAC tissues. Expression of both proteins was found in most cases: 80 out of the 107 for p-S6K1 (74.8%) and 87 of the 107 (81.3%) for Gli1 were positive (FIG. 6A), and there was a strong correlation between the levels of p-S6K1 and Gli1 (FIG. 6C). The inventors also collected 15 samples from rat Barrett's esophagus models (Yen et al., 2008), and found that there were no p-S6K1 and Gli1 signals in normal esophageal squamous cells, but observed strong signals of both p-S6K1 and Gli1 in 3 of 5 Barrett's esophagus (BE) and 3 of 5 EAC tissue samples (FIG. 14E). Together, these data further support the notion that the activation of mTOR/S6K1 and Gli1 pathways is involved in the transformation of the esophagus. To ensure the Gli1S84 phosphorylation also exists in human EAC tumor tissues, the inventors first tested the applicability of the anti-p-Gli1S84 antibody for IHC. The inventors found that the staining of p-Gli1 could be blocked by phosphorylated Gli1 peptide used for developing antibody, but not by a non-phosphorylated paired peptide (FIG. 14F). Moreover, using the same set of mouse colon slides used above, the inventors could not detect any signal of p-S6K1, and as expected, the signal of p-Gli1 was also negative (FIG. 14A, middle and right panels). Therefore, the p-Gli1 antibody is applicable for IHC. The inventors then examined the Gli1, p-Gli1, and p-S6K1 in human EAC tissue microarray (n=70), and the result again showed that there was a strong positive correlation between p-S6K1 and Gli1 or p-Gli1 (FIGS. 14G and 6D-6F). All p-Gli1-positive tissues are also Gli1-positive, and among the Gli1-positive tissues, there was a strong positive correlation between p-Gli1 and p-S6K1 (FIG. 6G). Thus, the phosphorylation of Gli1 also exists in human EAC tumor tissues. Additionally, using human tissue microarray with multiple cancer types, the inventors found a positive correlation between p-S6K1 and Gli1 (FIGS. 14H and 14I), suggesting that the regulation of Gli1 by S6K1 might be not limited to EAC, and is worthwhile to be tested in multiple kinds of cancers in the future.

Example 6

Figures 15A, 15B, 15C:
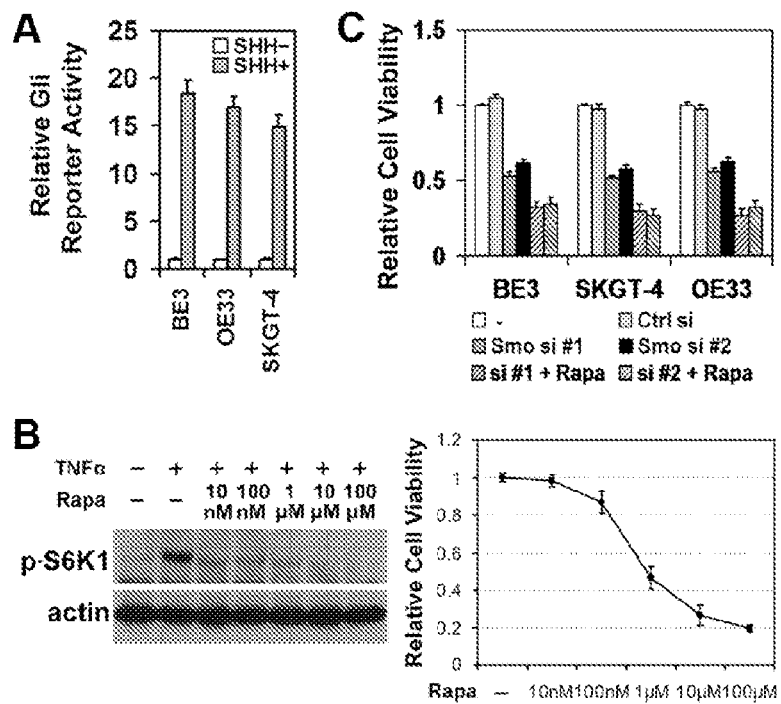
FIGS. 15A-15C. related to FIG. 7. The effects of mTOR and/or HH pathway inhibitors on EAC cells.

A Combination Therapy that Targets Both Canonical HH and mTOR/S6K1/Gli1 Pathways in EAC Cells Provides Better Therapeutic Effects Consistent with the previous reports (Berman et al., 2003; Sims-Mourtada et al., 2006), the inventors detected the activated form of SHH protein, the amino terminal domain of SHH (SHH-N) (Ng and Curran, 2011), in the EAC cell lines (FIG. 7A). In addition, SHH treatment dramatically increased expression of the Gli reporter (FIG. 15A) and Gli1 target genes (FIG. 7B). Hence, the EAC cell lines exhibit activated canonical HH pathway. Because the inventor's data have shown that in EAC cell lines mTOR/S6K1-mediated Gli1 activation is SMO-independent, the inventors speculated that mTOR/S6K1/Gli1 should enhance the resistance of EAC cells to SMO inhibitors. As expected, the IC$_{50}$ value of cyclopamine or GDC-0449 in BE3/S84E was much higher than that for BE3/EV, BE3/Gli1, and BE3/S84A (FIG. 7C). Moreover, TNFα treatment increased the resistance of BE3/Gli1, but not BE3/S84A, to cyclopamine or GDC-0449 (FIG. 7D), suggesting that Gli1S84 phosphorylation enhances cell resistance to SMO inhibitors. Then, the inventors examined whether a combination of inhibitors of HH and mTOR pathways would be more effective for these EAC cell lines. To avoid the killing effect of rapamycin, the inventors first determined that 10 nM rapamycin was sufficient to inhibit the activation of S6K1 in BE3 cells but did not significantly inhibit cell viability (FIG. 15B). Thus, the inventors used 10 nM rapamycin for all subsequent experiments. The inventors found that rapamycin treatment enhanced the efficacy of cyclopamine or GDC-0449 in the EAC cell lines (FIG. 7E). Moreover, knock-down of SMO also inhibited cell viability, and rapamycin treatment further enhanced the inhibitory effect (FIG. 15C). Interestingly, the effects of rapamycin on SMO inhibitors existed in BE3/Gli1 cells, but not in BE3/S84E cells (FIG. 7F). Therefore, an mTOR inhibitor could enhance the effects of a SMO inhibitor in vitro through eliminating the phosphorylation of Gli1S84. For further examining the crosstalk between the mTOR and HH pathways in vivo, the inventors performed in vivo combination therapy using GDC-0449 and another mTOR inhibitor, RAD-001, which is widely used in combination with other anti-tumor drugs in clinical trials (Piguet et al., 2011; Price et al., 2010; Quek et al., 2011). The inventors subcutaneously inoculated mice with BE3 cells and treated them with GDC-0449, RAD-001, or both, and found that though low dose RAD001 did not inhibit tumor growth, it enhanced the tumor-inhibitory effect of GDC-0449 (FIG. 7G). Therefore, the combination of the inhibitors targeting the two pathways could produce better efficacy for targeted therapy.

Example 7

SMO-Independent Activation of Gli1 by AKT and ERK Requires mTOR/S6K1

Figure 16:
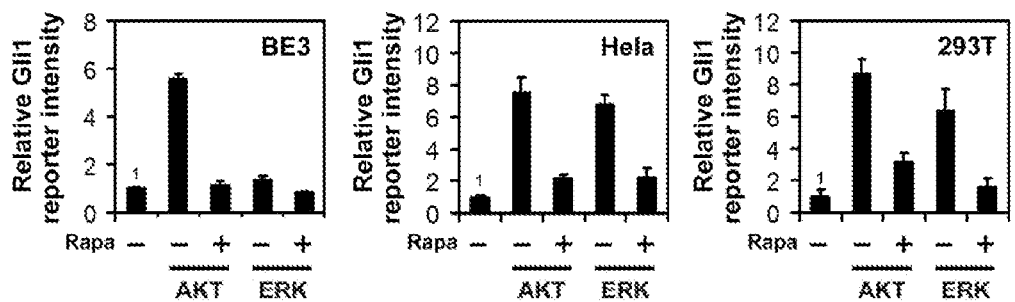
FIG. 16. related to FIG. 8. AKT and ERK can activate Gli1 through mTOR/S6K1 pathway. The listed cell lines were transfected with AKT or ERK in combination with Gli-Luciferase and CMV-Renilla reporters followed by treatment with rapamycin (50 nM) for 24 hr. Then, the luciferase assay was performed to measure the expression of Gli reporter in all treated cells. Error bars represent SD (n=3).

It has been reported that AKT and MAPK/ERK also activate the HH pathway in a SMO-independent manner. Interestingly, AKT and ERK can activate the mTOR/S6K1 pathway by inhibiting the TSC1/2 complex (Lee et al., 2007a; Ma et al., 2005; Ozes et al., 2001). This prompted us to test if the mTOR/S6K1 pathway is required for the activation of Gli1 by the two kinases. Through ectopic expression of AKT or ERK, the inventors found that Gli1 activity increased, which could be blocked by rapamycin (FIG. 16). Moreover, the activation of AKT or ERK also stimulated the phosphorylation of S6K1T389 and Gli1 Ser84, which was inhibited by rapamycin (FIG. 8A). However, AKT and ERK lost the ability to induce Gli1 phosphorylation when S6K1 was knocked down (FIG. 8B). Therefore, our results indicated that mTOR/S6K1/Gli1 pathway might mediate the previously reported AKT and ERK-stimulated Gli1 activation (FIG. 8C).

Example 8

Figure 17:
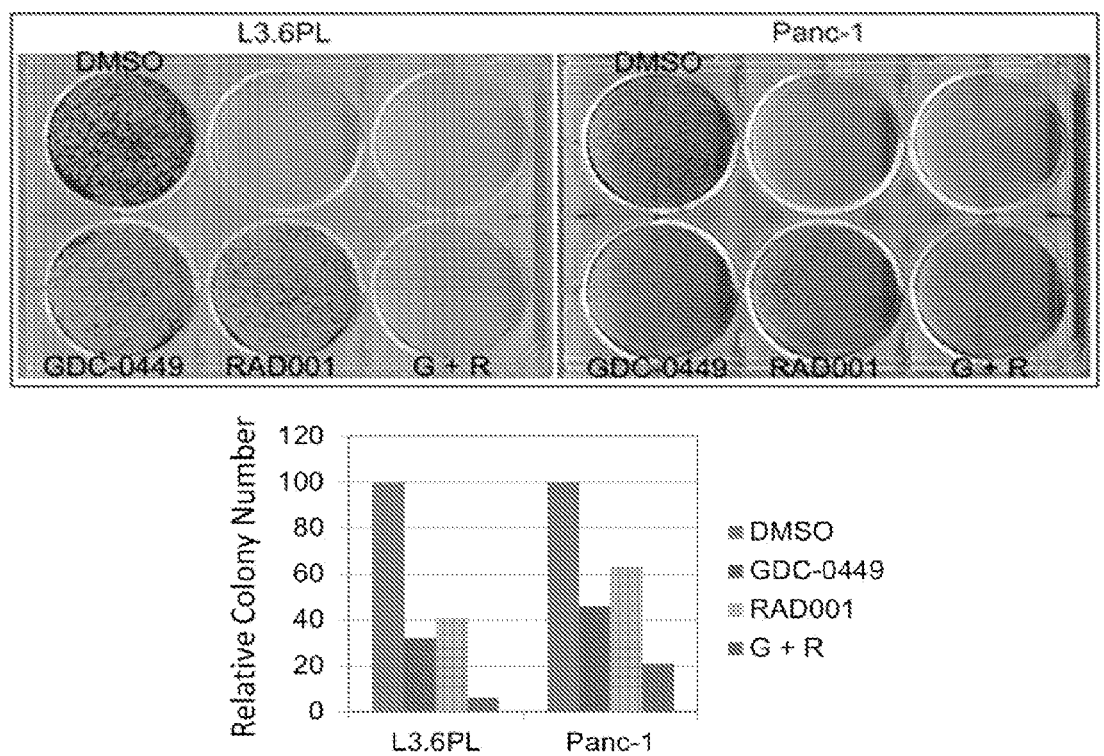
FIG. 17. Combinations of inhibitors targeting Hedgehog and mTOR pathways show a more potent inhibitory effect on pancreatic cancer cell growth. Inhibitors (GDC-0449 and RAD001) were used either alone or in combination to treat PDAC cell lines L3.6PL and Panc-1. DMSO was used as a negative control. Cell colony numbers were counted and results graphed. Treatments indicated in each graph are (from left to right) DMOS, GDC-0449, RAD001, and G+R.

Gli1 is a Marker for the Non-Canonical HH Pathway and Gli2 is a Marker for the Canonical HH Pathway To show that using combinations of inhibitors targeting the HH and mTOR pathways yields a more potent inhibitory effect on pancreatic cancer cell growth, such inhibitors (i.e. GDC-0449 and RAD001) were used either alone or in combination to treat PDAC cell lines L3.6PL and Panc-1. DMSO was used as a negative control. Cell colony numbers were counted (FIG. 17) for each condition.

Figure 18:
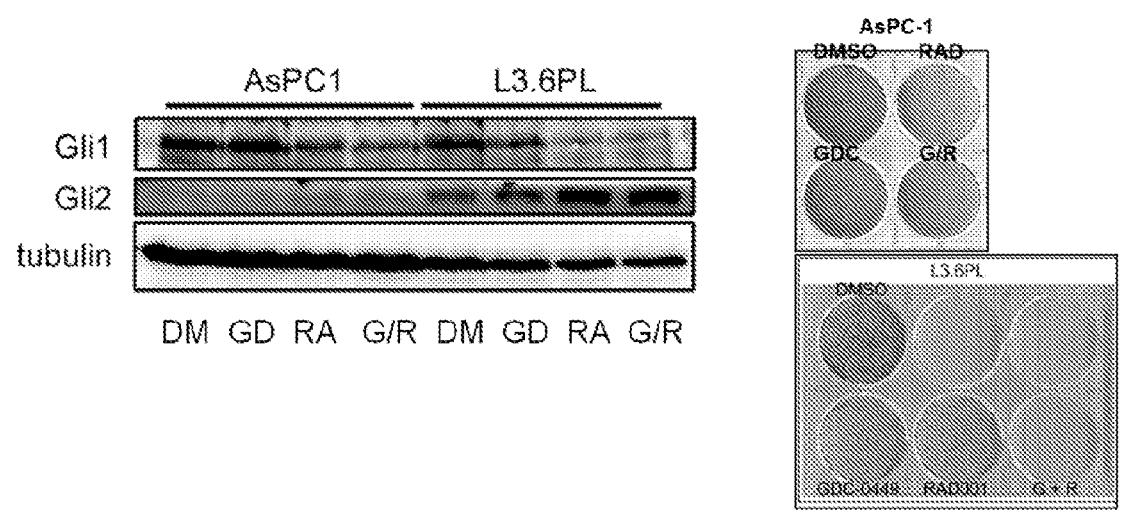
FIG. 18. Gli2 is a marker for the activity of canonical Hedgehog pathway and is negatively regulated by Gli1. Inhibitors (GDC-0449 and RAD001) were used either alone or in combination to treat L3.6PL and AsPC-1 cells. DMSO was used as a negative control. The combination of RAD001 and GDC-0449 works better for L3.6PL cells than AsPC-1 cells. Right panel shows cell colony numbers. Left panel shows a western blot of Gli1 and Gli2, with a blot of tubulin as a loading control.

Inhibitors (GDC-0449 and RAD001) were used either alone or in combination to treat L3.6PL and AsPC-1 cells. DMSO was used as a negative control. Cell colony numbers were counted and a western blot of Gli1 and Gli2 was performed (FIG. 18). The combination of RAD001 and GDC-0449 worked better for L3.6PL cells than AsPC-1 cells. Therefore, Gli2 is a marker for the activity of the canonical HH pathway and is negatively regulated by Gli1.

Knock-down of Gli1 in PDAC cells sensitized the cells to gemcitabine (GEM), and overexpression of Gli1 protected PDAC cells from GEM. The inventor's performed a western blot for Gli1 in stable clones of AsPC-1 and CF-Pac-1 cells with Gli1 knocked down or ectopically expressed (FIG. 19A). MTT assays were performed on CF-Pac-1 stable clones (FIG. 19B) and AsPC-1 stable clones (FIG. 19C) with GEM. Gli1 expression correlated negatively with sensitivity of pancreatic cancer cells to GEM.

Human PAC xenografts show different kinase patterns. Therefore, the expression of Gli1 in human PDAC xenografts from the HIM mouse model is potentially regulated by kinase expression. Gli1 might be regulated by different pathways in tumor tissues from different patients. A western blot was performed of S6K1, phosphorylated S6K1, Gli1, IKK-alpha, IKK-beta, ERK, phosphorylated ERK, and beta-actin (FIG. 20).

A western blot was performed to show the effect of PF-4708671 on S6 phosphorylation, S6K1 phosphorylation, and Gli1 expression in the BT549 cell line (FIG. 21). Gli1 expression was decreased by treatment with PF-4708671, a S6K1 inhibitor, indicating that Gli1 was also correlated with S6K1 in breast cancer cell lines.

AKT inhibitor (MK) and mTOR inhibitor (R), which inhibits S6K1 activation, decreased Gli1 protein levels in BT549 and Hs578t breast cancer cells (FIG. 22, see black boxes). A western blot was performed for Gli1, phosphorylated AKT, phosphorylated S6K1, phosphorylated ERK, and actin in BT549 and Hs578t cells after treatment with an mTOR inhibitor (R), an AKT inhibitor (MK), an HH inhibitor (G), or an ERK inhibitor (AZD).

AKT inhibitors and mTOR inhibitors, which inhibit S6K1 activation, decreased Gli1 protein levels in MDA-MB-231 breast cancer cells (FIG. 23, see black box). Therefore, Gli1 is a marker for the non-canonical HH pathway and Gli2 is a marker for the canonical HH pathway (FIG. 24).

Example 9

Experimental Procedures

Human Tissues

Human EAC specimens for immunohistochemistry were obtained retrospectively from patients undergoing, as primary treatment, complete esophageal surgical resection at MD Anderson Cancer Center (MDACC) between January 1986 and December 1997. This project was approved by the Institutional Review Board. The multiple tissue microarrays were purchased from US Biomax, Inc (BC00112 and MTU241).

Immunoprecipitation, Immunoblotting, and In Vitro Kinase Assays

Immunoprecipitation and immunoblotting were performed as previously described (Lee et al., 2007a). For in vitro kinase assays, BL21 competent cells were transformed with pGEX-6P-1 vector, pGEX-6P-1-S6, pGEX-6P-1-Gli1F1, or pGEX-6P-1-Gli1F2, and after growth overnight, the cells were lysed and the target proteins were purified using GST antibody crosslinked agarose beads (Thermo Scientific) according to the manufacturer's instruction. In addition, 90% confluent BE3 cells were transfected with HA-S6K1, HA-S6K1T389E, HA-S6K1T389A, or HA-S6K1K100R, and 24 hr after transfection, the cells were lysed and immunoprecipitated with anti-HA antibody. Purified GST protein or GST fusion proteins were incubated with purified HA-S6K1 or HA-S6K1 mutants in the presence of 50 mM ATP in a kinase buffer for 30 min at 30° C. Reaction products were subjected to SDS-PAGE and then blotted with phosphor-Thr/Ser antibody.

$IC_{50}$ Evaluation for Cyclopamine and GDC-0449

Cells were seeded in 96-well plates at the density of 5000 cells/well, and after overnight growth, the cells were exposed to increasing concentrations ranging from 1 nM to 100 μM for cyclopamine or GDC-0449, with or without 10 nM rapamycin, for 48 hr. The concentrations required to inhibit cell growth by 50% ($IC_{50}$) were calculated from survival curves.

Rat Model of BE and EAC

The rat model was established as previously described (Yen et al., 2008). The excised esophageal tissues from normal esophagus, BE, or EAC were fixed in 10% buffered formalin for 24 h and then transferred to 80% ethanol. The tissue was longitudinally divided into slices for immunohistochemistry staining.

Tumorigenicity Assay and Combination Therapy In Vivo

All animal procedures were conducted under the guidelines approved by the Institutional Animal Care and Use Committee (IACUC) at M.D. Anderson Cancer Center. Female nude mice were housed under standard conditions. For tumorigenicity assay, $1\times10^6$ BE3 stable cells were subcutaneously injected in right flank. The resulting tumors were measured with calipers weekly, and tumor volume was determined using the formula: $l\times w^2$, where l is the longest diameter and w is the shortest diameter. For combination therapy, $1\times10^6$ BE3 cells were subcutaneously injected in right flanks of nude mice and allowed to grow for 10 days before drug treatment. GDC-0449 was formulated in MCT (0.5% methylcellulose and 0.5% Tween 80), and RAD001 in water. GDC-0449 (50 mg/kg) and RAD001 (10 mg/kg) were dosed qd by oral gavage. The tumors were measured with calipers every 4 days. Data were presented as tumor volume (mean±SD). Statistical analysis was done using the Student's t-test by the program SPSS for Windows.

Antibodies and Reagents

The antibodies used in this study were anti-4E-BP1 (#9452, Cell Signaling Technology), anti-actin (#A2066, Sigma), anti-AKT (#9272, Cell Signaling Technology), anti-p-Akt (S473) (#9271, Cell Signaling Technology), anti-Erk1/2 (#9102, Cell Signaling Technology), anti-p-Erk1/2 (Thr202/Tyr204) (#9106, Cell Signaling Technology), anti-flag (#F3165, Sigma), anti-Gli1 for IP and Western blot analyses (#2534, Cell Signaling Technology), anti-Gli1 for immunostaining (#sc-20687, Santa Cruz Biotechnology), which has been further validated through siRNA-mediated knock-down as well as peptide blocking immunohistochemistry (data not shown), anti-Gli2 (#ab26056, Abcam), anti-Gli3 (#AF3690, R&D system), anti-HA (#12CA5, Roche Applied Science), anti-patched (#ab39266, Abcam), anti-lamin B (#sc-56145, Santa Cruz Biotechnology), anti-mTOR (#2972, Cell Signaling Technology), anti-raptor (#09-217, Millipore), anti-rictor (#sc-50678, Santa Cruz Biotechnology), anti-p-S6 (#4857, Cell Signaling Technology), anti-S6K1 (#sc-230, Santa Cruz Biotechnology), anti-p-S6K1 (T389) for western (#9205, Cell Signaling Technology), anti-p-S6K1 (T389) for immunostaining (#04-392, Millipore), anti-p-Ser/Thr (#612548, BD Biosciences), anti-SHH-N (#MAB464, R&D system), anti-smoothened (#ab72130, Abcam), anti-SuFu (#2522, Cell Signaling Technology), anti-TSC1 (#4963, Cell Signaling Technology), anti-TSC2 (#sc-893, Santa Cruz Biotechnology), and anti-tubulin (#T5168, Sigma). The antibody against the phosphorylation of Gli1S84 was produced using the synthetic phosphorylated peptides KLTKKRALpSISPLSDA (Peptide 2.0 Inc, Chantilly, Va.) as antigen and purified on a phosphopeptide column (EZBiolab Inc, Carmel, Ind.). Human TNFα was from Roche Applied Science; Rapamycin and cyclopamine were from LC Laboratories; GDC-0449, RAD001, and WYE-354 were from Selleck Chemicals LLC (Houston, Tex.); Recombinant human sonic hedgehog (rh-SHH) was from R&D systems (#1845-SH-025); Dual-luciferase assay kit was from Promega; Lipofectamine 2000 and antifade reagent with DAPI were from Invitrogen.

Plasmids, siRNA, and shRNA

Full-length Gli1 was generated from pflag-CMV2-Gli1 (a kind gift from Dr. Oro) using KOD plus DNA polymerase (TOYOBO, Japan), and then inserted into pcDNA3 (Invitrogen) for stable transfection and p3flag-CMV10 (Sigma) for transient transfection. The myc tagged SuFu-expressing plasmid was from Dr. Toftgård. The Gli1-reporter plasmid (GliBS) and mutant Gli1-reporter plasmid (mGliBS) were kindly provided by Dr. Sasaki. The plasmids of mTOR, mTOR 2035T, HA-S6K1, AKT, and ERK were described in the inventor's previous work (Ding et al., 2005; Lee et al., 2007). The site mutants of Gli1S84 (S84E and S84A), S6K1T389 (T389E and T389A), and S6K1K100 (K100R) were generated by using the Quick Change multi site-directed mutagenesis kit from Stratagene (La Jolla, Calif.). The fragment 1 of Gli1 (Gli1F1) including the first 500 amino acids and the Gli1F2 including the other amino acids were acquired through PCR and inserted in pGEX-6P-1 (GE Healthcare) for constructing GST fusion protein, i.e. GST-Gli1F1 and GST-Gli1F2. The GST-S6 as S6K1 substrate positive control was described in our previous work (Lee et al., 2007). The shRNA targeting Gli1, Gli2, or Gli3 was constructed in pSilencer (Ambion) through inserting the corresponding oligonucleotides as below: Gli1 shRNA #1, CTTTGATCCTTACCTCCCA (SEQ ID NO: 3); Gli1 shRNA #2, AGCTCCAGTGAACACATAT (SEQ ID NO: 4); Gli2 shRNA #1, CTCGCTAGTGGCCTACATC (SEQ ID NO: 5); Gli2 shRNA #2, TGGGACTGGCAGCCCATCC (SEQ ID NO: 6); Gli3 shRNA #1, CGGAAATCAATAG-GAGTTG (SEQ ID NO: 7); Gli3 shRNA #2, CGAAGGAACAACCCTTGTC (SEQ ID NO: 8); control shRNA, CGTACGCGGAATACAACGA (SEQ ID NO: 9). Lentivirus-carried shRNA system targeting Gli1 for establishing stable clones were in pGIPZ vector and purchased from Thermo Scientific (Catalog No.: RHS4531-NM_005269). S6K1 SMARTpool siRNA and siRNA targeting the 3' UTR were purchased from Dharmacon RNA Technologies. Pre-designed siRNA oligonucleotides were purchased from Sigma (#00148505 and #00148506 for targeting Gli1, #00203144 and #00203146 for targeting mTOR, #0048380 and #00048381 for targeting raptor, #00223573 and #00366683 for targeting rictor, and #00157741 and #00157742 for targeting smoothened.

Cell Culture and Transfection

Human esophageal cancer cell lines, BE3, SKGT4, OE33 (Boonstra et al., 2010; Yen et al., 2008), 293T, Hela, HT29, SKOV3, A549, MCF-7, MDA-MB-231, and HepG2 cells were maintained at 37° C. in a 5% $CO_2$ incubator with DMEM/F12 or RPMI 1640 plus 10% fetal bovine serum (FBS). For serum starvation, the cells were cultured in DMEM/F12 without FBS overnight before further treatment. The amino acid starvation was performed as described by Nicklin et al. (Nicklin et al., 2009). The plasmids and siRNA were transfected using Lipofectamine 2000 according to the manufacturer's instruction. For transient transfection, the cells were harvested for mRNA extraction after 24 hr of transfection or for protein extraction after 48 hr of transfection, or used for luciferase assay after transfection for 24 hr (cDNA) or 48 hr (RNA interference). For stable transfection, the cells were subjected to G418 selection after 24 hr of transfection.

Luciferase Assay

Cells were seeded in six-well plates and transfected with GliBS or mGliBS combined with CMV-Renilla vector as an internal standard. After overnight (12-16 hr) transfection, the cells were used for further experiments. After treatment, the cells were rinsed with PBS and subjected to luciferase assay using a dual-luciferase reporter assay system (Promega) based on the manufacturer's instruction.

Real-Time PCR Analysis

Total RNA was extracted from cells by TRIzol (Invitrogen, Carlsbad, Calif., USA) and processed directly to cDNA by reverse transcription using Superscript III kit (Invitrogen, Carlsbad, Calif., USA). The PCR reactions were performed in triplicate with iQ SYBR™ Green Supermix (BIORAD, Hercules, Calif., USA) in an iCycler iQ system (Bio-Rad). The mRNA levels of target genes were normalized to that of β-actin according to the Ct value-based methods described by Wang et al (Wang et al., 2007). Primers for the genes tested in the present experiments are listed in Table 1 in the Supplemental Information (Table 1), and for each gene, the forward primer and reverse primer were designed according to target genes located in the different exons to monitor genomic DNA contamination. After reaction, the PCR products were subjected to electrophoresis to ensure the amplification from mRNA but not contaminated genomic DNA. Paired t-test was adopted to study the expressions of target genes.

TABLE 1

Primers for real-time PCR

| Genes | GenBank No. | | Primer sequence |
|---|---|---|---|
| N-MYC | NM_005378.4 | FP: | GCAGAATCGCCTCCGGATCC (SEQ ID NO: 10) |
| | | RP: | ACGTGGAGCAGCTCGGCATC (SEQ ID NO: 11) |
| CCND1 | NM_053056.2 | FP: | AGAAGGAGGTCCTGCCGTCC (SEQ ID NO: 12) |
| | | RP: | GGTCCAGGTAGTTCATGGCC (SEQ ID NO: 13) |
| PTCH1 | NM_001083602.1 | FP: | TCGAGACCAACGTGGAGGAG (SEQ ID NO: 14) |
| | | RP: | CCCAGTCCAGGTGTTGTAGG (SEQ ID NO: 15) |
| GLI1 | NM_005269.2 | FP: | CCAGCCAGAGAGACCAACAG (SEQ ID NO: 16) |
| | | RP: | GTGCGGATAACCGTCTGCAG (SEQ ID NO: 17) |
| ACTIN | NM_001101.3 | FP: | CGAGCACAGAGCCTCGCC (SEQ ID NO: 18) |
| | | RP: | GCGAAGCCGGCCTTGCAC (SEQ ID NO: 19) |

FP: Forward Primer;
RP: Reverse Primer.

Cellular Fractionation

Cellular fractionation was performed as described previously (Lin et al., 2001). Briefly, cells were lysed in the lysis buffer (20 mM HEPES, pH 7.0, 10 mM KCl, 2 mM $MgCl_2$, 0.5% NP-40, 1 mM $Na_3VO_4$, 10 mM NaF, 1 mM PMSF, 2 μg/mL aprotinin). The lysate was centrifuged at 1500 g for 5 min to sediment the nuclei. The supernatant was then centrifuged at a maximum speed of 16,100 g for 20 min, and the resulting supernatant formed the non-nuclear fraction. The nuclear pellet was washed three times with lysis buffer to remove any contamination from cytoplasmic membranes. To extract nuclear proteins, the isolated nuclei were resuspended in NETN buffer (150 mM NaCl, mM EDTA, 20 mM Tris-Cl, pH 8.0, 0.5% NP-40, 1 mM Na3VO4, 10 mM NaF, 1 mM PMSF, and 2 μg/mL aprotinin), and the mixture was sonicated briefly. Nuclear lysates were collected after centrifugation at 16,100 g for 20 min at 4° C.

In-Gel Digestion for Mass Spectrometric Analysis

Overnight serum-starved BE3 cells were treated for 6 hr with TNFα directly or following rapamycin pretreatment for 2 hr. Cells were then harvested for protein extraction, and endogenous Gli1 was immunoprecipitated using anti-Gli1 antibody (#2534, Cell Signaling Technology) from the cell lysate. The IP samples were subjected to SDS-PAGE electrophoresis followed by commassie blue staining. The band that corresponds to the Gli1 molecular weight was excised from the gel for in-gel digestion. The in-gel digestion method used in this study was a modification of that reported by Shevchenko (Shevchenko et al., 2006). Briefly, gel bands were excised into cubes ($1\times1\times1$ mm$^3$) and transferred into microcentrifuges tube prior to digestion. The gel pieces were washed and destained once in 25 mM ammonium bicarbonate (ABC), 5% ACN and twice in 25 mM ABC, 50% ACN. Then, neat acetonitrile was added and incubated until gel pieces shrink, after which all liquid was removed. Proteins were subsequently reduced in 10 mM DTT and alkylated in 55 mM iodoacetamide. Finally, the gel pieces were washed, dehydrated, and dried by a SpeedVac. Protein digestion was performed overnight at 37° C. in 10 mM ABC including 10 ng/μL of trypsin (Promega, Madison, Wiss.). After trypsin digestion, the supernatant was transferred into a microcentrifuge tube for additional peptide extraction by adding 60% ACN, 0.5% TFA for 5 min. The peptides were extracted twice, combined together, concentrated by SpeedVac to dry, and then subjected to Nanoscale capillary LC-MS/MS analysis.

Nanoelectrospray Mass Spectrometry

Nanoscale capillary LC-MS/MS analysis was performed using an Ultimate capillary LC system (LC Packings, Amsterdam, The Netherlands) coupled to a QSTARXL quadrupole-time of flight (Q-TOF) mass spectrometer (Applied Biosystem/MDS Sciex, Foster City, Calif.). The nanoscale capillary LC separation was performed on a RP C18 column (15 cm, 75 μm i.d.) with a flow rate of 200 nL/min and a 70 min linear gradient of 5%-50% buffer B. Buffer A contained 0.1% formic acid in 2% aqueous ACN; buffer B contained 0.1% formic acid in 98% aqueous ACN. A nanoelectrospray interface was used for LC-MS/MS analysis. Ionization (2.0 kV ionization potential) was performed with a coated nanoLC tip. The nanoLC tip used for on-line LC-MS was a PicoTip (FS360-20-10-D-20; New Objective, Cambridge, Mass.). The optimum sprayer position was typically flush with or slightly inserted (approximately 1 mm) into the curtain chamber. The temperature of the heated laminar flow chamber was set at 100° C. The potential of the curtain plate was set at 250 V and the curtain gas was set at 1.3 L/min. Data acquisition was performed by automatic Information Dependent Acquisition (IDA; Applied Biosystem/MDS Sciex). The IDA automatically finds the most intense ions in a TOF MS spectrum, and then performs an optimized MS/MS analysis on the selected ions. The product ion spectra generated by nanoLC-MS/MS were searched against NCBI databases for exact matches using the ProID program (Applied Biosystem/MDS Sciex) and the MASCOT search program (Hirosawa et al., 1993). A *Homo sapiens* taxonomy restriction was used, and the mass tolerance of both precursor ion and fragment ions was set to 0.3 Da. Carbamidomethyl cysteine was set as a fixed modification, while other modifications were set as variable modifications.

MTT, Anchorage-Independent Growth, Migration, and Invasion Assays 3-(4,5-Dimethylthiazol-2-yl)-2,5-diphenyltetrazolium bromide (MTT) and anchorage-independent growth of stable transfectants were assayed as previously described (Kuo et al., 2010). The migration and invasion assays were performed using a 24-well transwell plate (Corning, Mass.) according to the manufacturer's instruction.

Immunofluorescence and Immunohistochemistry

Immunohistochemical staining was performed as previously described (Yen et al., 2008). After incubation with biotin-conjugated secondary antibody and avidin-biotin-peroxidase complexes, the immunoreaction was visualized using the amino-ethylcarbazole chromogen. For single tissue slides, staining intensity was defined as undetectable (0) or detectable (1), and the extent of positive cancer cells with detectable pS6K1 and Gli1 staining was expressed as the fraction of labeled cells, i.e. labeling index (LI) in the cancer specimens. For TMA, staining intensity was calculated using the Dako Chroma® systems ACISIII®, and the results were analyzed as described before (Liao et al., 2009; Xuan et al., 2006). Fisher's exact test and Spearman rank correlation tests were used for statistical analysis; $P<0.05$ was considered statistically significant. The immunofluorescence of EAC cell lines was performed as previously described (Ding et al., 2005).

Statistical Analyses

Statistical analyses were performed with the Student's t-test, Spearman rank correlation test, or Fisher's exact test as indicated. A P-value of $<0.05$ was considered statistically significant. All data analyses were performed using the program SPSS for Windows.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the methods described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention.

REFERENCES

The following references, to the extent that they provide exemplary, procedural or other details supplementary to those set forth herein, are specifically incorporated herein by reference.

U.S. Pat. No. 6,656,963
U.S. Pat. Appln. No. 2008004287
WO05011700
Barnett et al., *Biochem. J.*, 385(Pt. 2):399-408, 2005.
Berman et al., Widespread requirement for Hedgehog ligand stimulation in growth of digestive tract tumours, *Nature*, 425:846-851, 2003.
Boonstra et al., Verification and unmasking of widely used human esophageal adenocarcinoma cell lines, *J. Natl. Cancer Inst.*, 102:271-274, 2010.
Brown et al., Control of p70 s6 kinase by kinase activity of FRAP in vivo, *Nature*, 377:441-446, 1995.
Buonamici et al., Interfering with resistance to smoothened antagonists by inhibition of the PI3K pathway in medulloblastoma, *Sci. Transl. Med.*, 2:51ra70, 2010.
Cheng and Yue, Role and regulation of human tumor suppressor SUFU in Hedgehog signaling, *Adv. Cancer Res.*, 101:29-43, 2008.

Dasmahapatra et al., *Clin. Cancer Res.*, 10(15):5242-52, 2004.

Di Marcotullio et al., Numb is a suppressor of Hedgehog signalling and targets Gli1 for Itch-dependent ubiquitination, *Nat. Cell Biol.*, 8:1415-1423, 2006.

Ding et al., Erk associates with and primes GSK-3beta for its inactivation resulting in upregulation of beta-catenin, *Mol. Cell*, 19:159-170, 2005.

Eksteen et al., Inflammation promotes Barrett's metaplasia and cancer: a unique role for TNFalpha, *Eur. J. Cancer Prev.*, 10:163-166, 2001.

Fukaya et al., Hedgehog signal activation in gastric pit cell and in diffuse-type gastric cancer, *Gastroenterology*, 131:14-29, 2006.

Gills and Dennis, *Expert Opin. Investig. Drugs*, 13:787-797, 2004.

Guertin and Sabatini, Defining the role of mTOR in cancer, *Cancer Cell*, 12:9-22, 2007.

Hildebrandt et al., Genetic variations in the PI3K/PTEN/AKT/mTOR pathway are associated with clinical outcomes in esophageal cancer patients treated with chemoradiotherapy, *J. Clin. Oncol.*, 27:857-871, 2009.

Hirosawa et al., MASCOT: multiple alignment system for protein sequences based on three-way dynamic programming, *Comput. Appl. Biosci.*, 9:161-167, 1993.

Holz et al., mTOR and S6K1 mediate assembly of the translation preinitiation complex through dynamic protein interchange and ordered phosphorylation events, *Cell*, 123:569-580, 2005.

Hongo et al., Epidemiology of esophageal cancer: Orient to Occident. Effects of chronology, geography and ethnicity, *J. Gastroenterol. Hepatol.*, 24:729-735, 2009.

Ingham and McMahon, Hedgehog signaling in animal development: paradigms and principles, *Genes Dev.*, 15:3059-3087, 2001.

Jemal et al., Cancer statistics, 2009, *CA Cancer J. Clin.*, 59:225-249, 2009.

Jenkins, Hedgehog signalling: emerging evidence for non-canonical pathways, *Cell Signal*, 21:1023-1034, 2009.

Jiang and Hui, Hedgehog signaling in development and cancer, *Dev. Cell*, 15:801-812, 2008.

Jin et al., *Br. J. Cancer*, 91:1808-1812, 2004.

Katoh and Katoh, Hedgehog signaling pathway and gastrointestinal stem cell signaling network (review), *Int. J. Mol. Med.*, 18:1019-1023, 2006.

Katoh and Katoh, Hedgehog target genes: mechanisms of carcinogenesis induced by aberrant hedgehog signaling activation, *Curr. Mol. Med.*, 9:873-886, 2009a.

Katoh and Katoh, Integrative genomic analyses on GLI1: positive regulation of GLI1 by Hedgehog-GLI, TGFbeta-Smads, and RTK-PI3K-AKT signals, and negative regulation of GLI1 by Notch-CSL-HES/HEY, and GPCR-Gs-PKA signals, *Int. J. Oncol.*, 35:187-192, 2009b.

Kolterud et al., Paracrine Hedgehog signaling in stomach and intestine: new roles for hedgehog in gastrointestinal patterning, *Gastroenterology*, 137:618-628, 2009.

Konings et al., The applicability of mTOR inhibition in solid tumors, *Curr. Cancer Drug Targets*, 9:439-450, 2009.

Kuo et al., ARD1 stabilization of TSC2 suppresses tumorigenesis through the mTOR signaling pathway, *Sci. Signal*, 3:ra9, 2010.

Lambert and Hainaut, Esophageal cancer: cases and causes (part I), *Endoscopy*, 39:550-555, 2007a.

Lambert and Hainaut, Esophageal cancer: the precursors (part II), *Endoscopy*, 39:659-664, 2007b.

Lee et al., IKK beta suppression of TSC1 links inflammation and tumor angiogenesis via the mTOR pathway, *Cell*, 130:440-455, 2007a.

Lee et al., MicroRNA-378 promotes cell survival, tumor growth, and angiogenesis by targeting SuFu and Fus-1 expression, *Proc. Natl. Acad. Sci. U.S.A.*, 104:20350-20355, 2007b.

Lee et al., Novel targets in esophageal and gastric cancer: beyond antiangiogenesis, *Expert Opin. Investig. Drugs*, 18:1351-1364, 2009.

Liao et al., Aberrant activation of hedgehog signaling pathway contributes to endometrial carcinogenesis through beta-catenin, *Mod. Pathol.*, 22:839-847, 2009.

Lin et al., Nuclear localization of EGF receptor and its potential new role as a transcription factor, *Nat. Cell Biol.*, 3:802-808, 2001.

Ma et al., Phosphorylation and functional inactivation of TSC2 by Erk implications for tuberous sclerosis and cancer pathogenesis, *Cell*, 121:179-193, 2005.

Metcalfe and de Sauvage, Hedgehog fights back: mechanisms of acquired resistance against Smoothened antagonists, *Cancer Res.*, 71:5057-5061, 2011.

Ng and Curran, The Hedgehog's tale: developing strategies for targeting cancer, *Nat. Rev. Cancer*, 11:493-501, 2011.

Nicklin et al., Bidirectional transport of amino acids regulates mTOR and autophagy, *Cell*, 136:521-534, 2009.

Nolan-Stevaux et al., GLI1 is regulated through Smoothened-independent mechanisms in neoplastic pancreatic ducts and mediates PDAC cell survival and transformation, *Genes Dev.*, 23:24-36, 2009.

Ohori, *Drug News Perspective*, 21(5):245-250, 2008.

Ozes et al., A phosphatidylinositol 3-kinase/Akt/mTOR pathway mediates and PTEN antagonizes tumor necrosis factor inhibition of insulin signaling through insulin receptor substrate-1, *Proc. Natl. Acad. Sci. U.S.A.*, 98:4640-4645, 2001.

Piguet et al., Everolimus augments the effects of sorafenib in a syngeneic orthotopic model of hepatocellular carcinoma, *Mol. Cancer Ther.*, 10:1007-1017, 2011.

Price et al., Phase II trial of gefitinib and everolimus in advanced non-small cell lung cancer, *J. Thorac. Oncol.*, 5:1623-1629, 2010.

Quek et al., Combination mTOR and IGF-1R inhibition: phase I trial of everolimus and figitumumab in patients with advanced sarcomas and other solid tumors, *Clin. Cancer Res.*, 17:871-879, 2011.

Richard et al., Recent advances in the development of selective, ATP-competitive inhibitors of mTOR, *Curr. Opin. Drug Discov. Devel.*, 13:428-440, 2010.

Sarkar and Li, *J. Nutr.*, 134(12 Suppl):3493S-3498S, 2004.

Sasaki et al., A binding site for Gli proteins is essential for HNF-3beta floor plate enhancer activity in transgenics and can respond to Shh in vitro, *Development*, 124:1313-1322, 1997.

Scales and de Sauvage, Mechanisms of Hedgehog pathway activation in cancer and implications for therapy, *Trends Pharmacol. Sci.*, 30:303-312, 2009.

Seto et al., Regulation of the hedgehog signaling by the mitogen-activated protein kinase cascade in gastric cancer, *Mol. Carcinog.*, 48:703-712, 2009.

Shevchenko et al., In-gel digestion for mass spectrometric characterization of proteins and proteomes, *Nat. Protoc.*, 1:2856-2860, 2006.

Sims-Mourtada et al., Hedgehog: an attribute to tumor regrowth after chemoradiotherapy and a target to improve radiation response, *Clin. Cancer Res.*, 12:6565-6572, 2006.

Stanton and Peng, Small-molecule modulators of the Sonic Hedgehog signaling pathway, *Mol. Biosyst.*, 6:44-54, 2010.

Stecca et al., Melanomas require HEDGEHOG-GLI signaling regulated by interactions between GLI1 and the RAS-MEK/AKT pathways, *Proc. Natl. Acad. Sci. U.S.A.*, 104:5895-5900, 2007.

Wang et al., Involvement of IFN regulatory factor (IRF)-1 and IRF-2 in the formation and progression of human esophageal cancers, *Cancer Res.*, 67:2535-2543, 2007.

Wiedmann and Caca, Molecularly targeted therapy for gastrointestinal cancer, *Curr. Cancer Drug Targets*, 5:171-193, 2005.

Wullschleger et al., TOR signaling in growth and metabolism, *Cell*, 124:471-484, 2006.

Xuan et al., Enhanced expression of hedgehog signaling molecules in squamous cell carcinoma of uterine cervix and its precursor lesions, *Mod. Pathol.*, 19:1139-1147, 2006.

Yang et al., *Cancer Res.*, 64:4394-4399, 2004.

Yen et al., Bile acid exposure up-regulates tuberous sclerosis complex 1/mammalian target of rapamycin pathway in Barrett's-associated esophageal adenocarcinoma, *Cancer Res.*, 68:2632-2640, 2008.

Zhu et al., *Oncogene*, 23:4984-4992, 2004.

Zoncu et al., mTOR: from growth signal integration to cancer, diabetes and ageing, *Nat. Rev. Mol. Cell Biol.*, 12:21-35, 2011.

The invention claimed is:

1. A method of treating a subject having a cancer or a gastrointestinal tract disease, comprising:
   a) selecting a subject having a cancer or a gastrointestinal tract disease, and who has been determined to have elevated S6K phosphorylation or Gli1 phosphorylation relative to a first reference level and elevated Gli1 expression or Gli1 nuclear localization relative to a second reference level, and administering a therapy comprising an SMO inhibitor and mTOR inhibitor to the subject;
   b) selecting a subject having a cancer or a gastrointestinal tract disease, and who has been determined to have elevated S6K phosphorylation or Gli1 phosphorylation relative to first reference level but not elevated Gli1 expression or Gli1 nuclear localization relative to a second reference level, and administering a therapy comprising an mTOR inhibitor but not an SMO inhibitor; or
   c) selecting a subject having a cancer or a gastrointestinal tract disease, and who has been determined to have an elevated Gli1 expression or nuclear localization relative to first reference level but not an elevated S6K phosphorylation or Gli1 phosphorylation relative to a second reference level, and administering a therapy comprising an SMO inhibitor but not an mTOR inhibitor.

2. The method of claim 1, further defined as a method of selecting a subject having a cancer or a gastrointestinal tract disease and who has been determined to have elevated S6K phosphorylation or Gli1 phosphorylation relative to a first reference level and elevated Gli1 expression or Gli1 nuclear localization relative to a second reference level, and administering a therapy comprising an SMO inhibitor and mTOR inhibitor to the subject.

3. The method of claim 1, further defined as a method of selecting a subject having a cancer or a gastrointestinal tract disease and who has been determined to have elevated S6K phosphorylation or Gli1 phosphorylation relative to first reference level but not elevated Gli1 expression or Gli1 nuclear localization relative to a second reference level, and administering a therapy comprising an mTOR inhibitor but not an SMO inhibitor.

4. The method of claim 1, further defined as a method of selecting a subject having a cancer or a gastrointestinal tract disease and who has been determined to have elevated Gli1 expression or nuclear localization relative to first reference level but not elevated S6K phosphorylation or Gli1 phosphorylation relative to a second reference level, and administering a therapy comprising an SMO inhibitor but not an mTOR inhibitor.

5. The method of claim 1, wherein the SMO inhibitor is GDC-0449, Cyclopamine, IPI-926, or BMS-833923 (XL139).

6. The method of claim 1, wherein the mTOR inhibitor is Rapamycin, WYE354, RAD001 or AP23573.

7. The method of claim 1, wherein the mTOR inhibitor is an S6K1 (p70 ribosomal S6 kinase 1) inhibitor.

8. The method of claim 1, wherein the mTOR inhibitor is an AKT inhibitor.

9. The method of claim 1, wherein the mTOR inhibitor is an ERK (extracellular signal-regulated kinase) inhibitor.

10. The method of claim 1, wherein the mTOR inhibitor is an IKKβ inhibitor (inhibitor of nuclear factor kappa-B kinase subunit beta).

11. The method of claim 1, wherein the gastrointestinal tract disease is an esophageal tumor or Barrett's esophagus.

12. The method of claim 1, wherein the cancer is breast cancer or pancreatic cancer.

13. A method of treating Barrett's esophagus (BE), comprising administering a therapy comprising a SMO inhibitor and mTOR inhibitor to a subject having Barrett's esophagus.

* * * * *

UNITED STATES PATENT AND TRADEMARK OFFICE
CERTIFICATE OF CORRECTION

PATENT NO. : 9,655,909 B2  
APPLICATION NO. : 14/371062  
DATED : May 23, 2017  
INVENTOR(S) : Mien-Chie Hung, Yan Wang and Jaffer Ajani Page 1 of 1

It is certified that error appears in the above-identified patent and that said Letters Patent is hereby corrected as shown below:

In Claim 13, Column 49, Lines 13-14, delete "a SMO inhibitor and mTOR inhibitor" and insert --GDC-0449 and RAD001-- therefor.

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*